(12) United States Patent
Freeman

(10) Patent No.: US 6,653,124 B1
(45) Date of Patent: Nov. 25, 2003

(54) ARRAY-BASED MICROENVIRONMENT FOR CELL CULTURING, CELL MONITORING AND DRUG-TARGET VALIDATION

(75) Inventor: Alex R. Freeman, Plano, TX (US)

(73) Assignee: Cytoplex Biosciences Inc., Dallas, TX (US)

( * ) Notice: Subject to any disclaimer, the term of this patent is extended or adjusted under 35 U.S.C. 154(b) by 188 days.

(21) Appl. No.: 09/710,700

(22) Filed: Nov. 10, 2000

(51) Int. Cl.[7] .................................................. C12M 1/12
(52) U.S. Cl. .............................. 435/297.1; 435/286.5; 435/288.5; 435/288.7; 435/305.2
(58) Field of Search ........................... 435/297.5, 286.5, 435/287.1, 287.2, 288.4, 288.5, 288.7, 297.1, 305.2

(56) References Cited

U.S. PATENT DOCUMENTS

| | | | |
|---|---|---|---|
| 4,839,292 A | 6/1989 | Cremonese | 435/313 |
| 5,721,135 A | 2/1998 | Thastrup et al. | 435/286 |
| 5,763,266 A | 6/1998 | Palsson et al. | 435/289 |
| 5,856,174 A * | 1/1999 | Lipshutz et al. | 435/286.5 |
| 5,888,807 A | 3/1999 | Palsson et al. | 435/293 |
| 5,958,762 A * | 9/1999 | Stoppini et al. | 435/297.5 |
| 5,976,813 A | 11/1999 | Beutel et al. | 435/7.1 |
| 6,001,585 A | 12/1999 | Gramer | 435/29 |
| 6,046,002 A | 4/2000 | Davis et al. | 435/6 |
| 6,099,803 A | 8/2000 | Ackley et al. | 422/68.1 |
| 6,197,575 B1 * | 3/2001 | Griffith et al. | 435/288.4 |
| 6,416,952 B1 * | 7/2002 | Pirrung et al. | 435/6 |

* cited by examiner

Primary Examiner—David A. Redding
(74) Attorney, Agent, or Firm—Jing-Hong DeJong

(57) ABSTRACT

An apparatus and method for cell culture in microchambers that are formed on or adjacent to a substrate. The microchambers are connected by one or more fluid conduits, valves and reagent reservoirs, is disclosed.

41 Claims, 5 Drawing Sheets

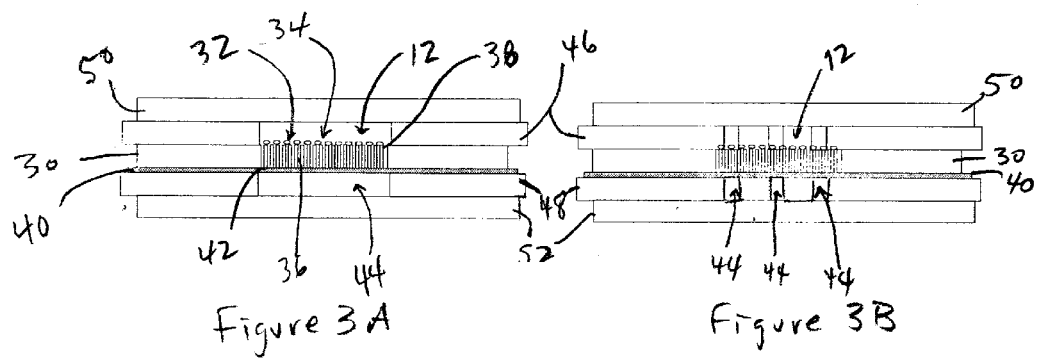
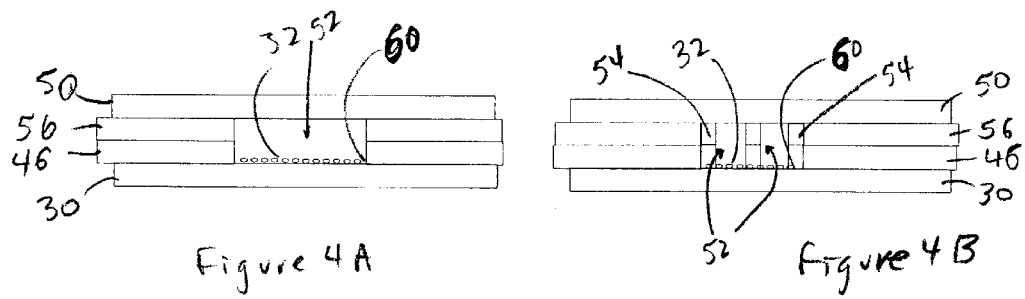
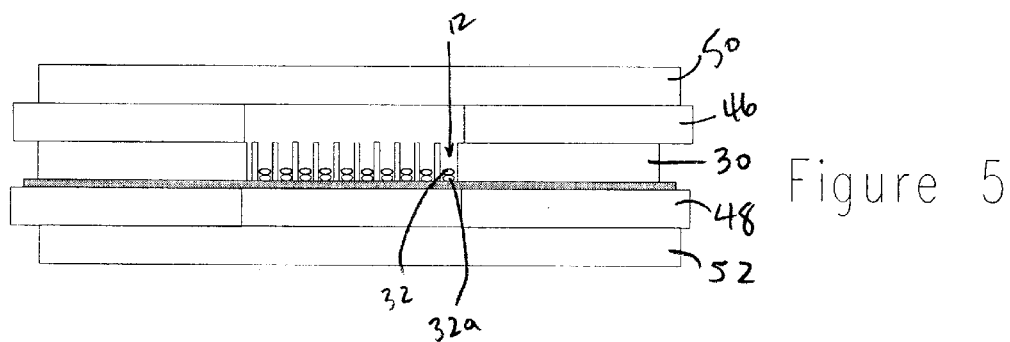

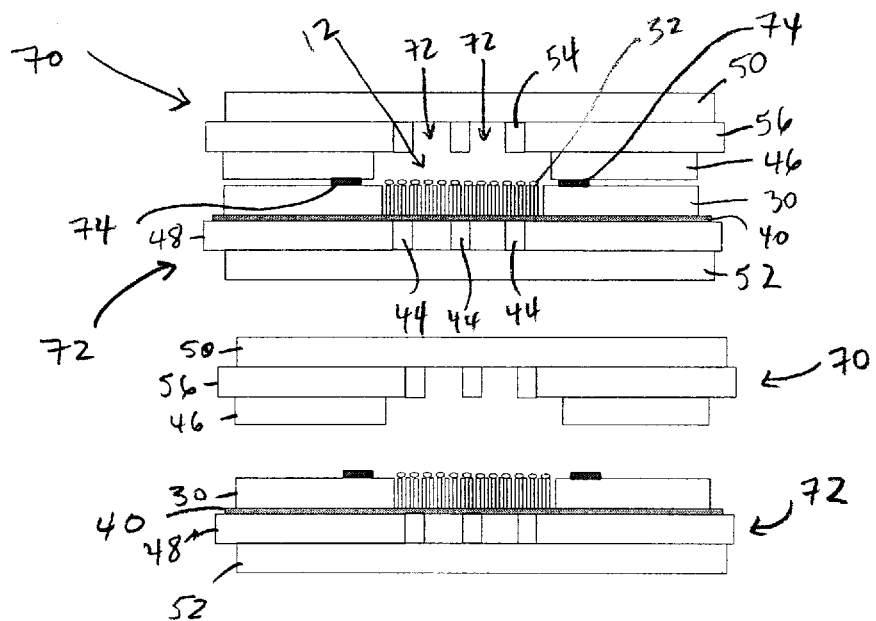
Figure 6
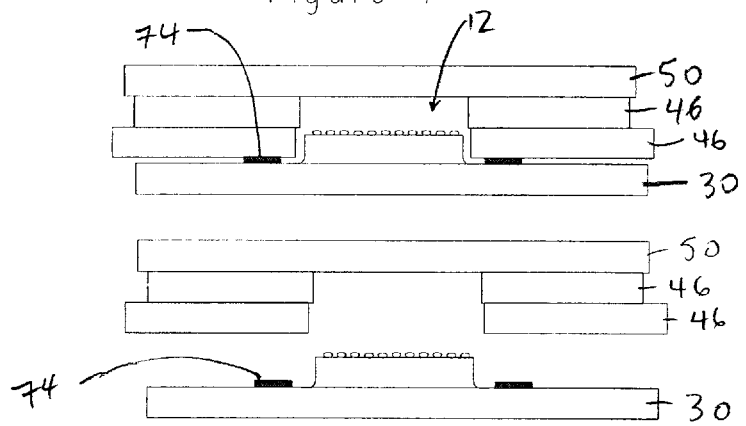
Figure 7
Figure 8
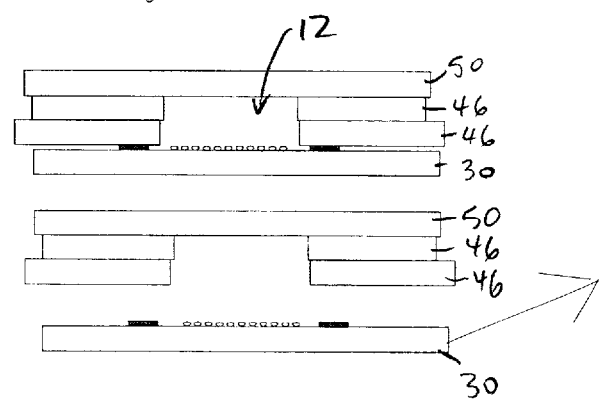
Figure 9
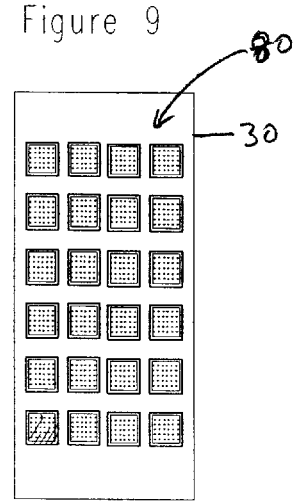

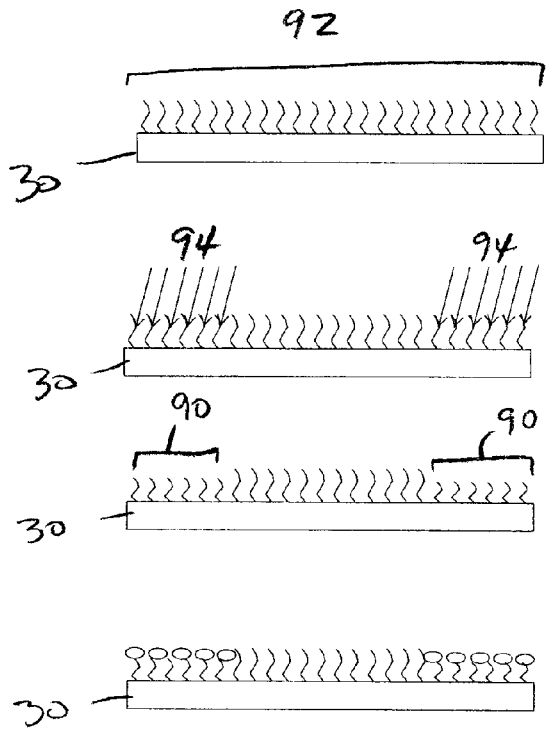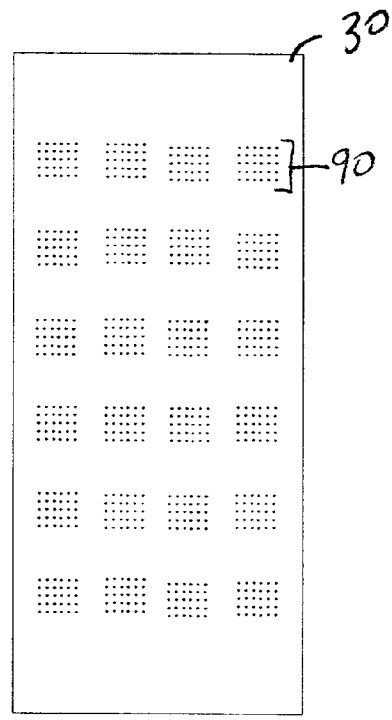
Figure 10
Figure 11
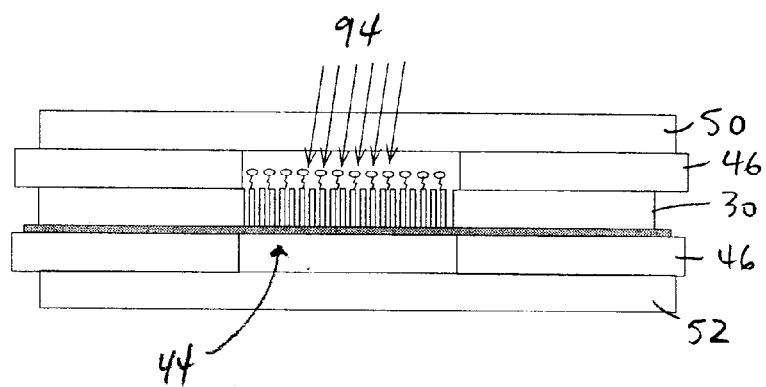
Figure 12

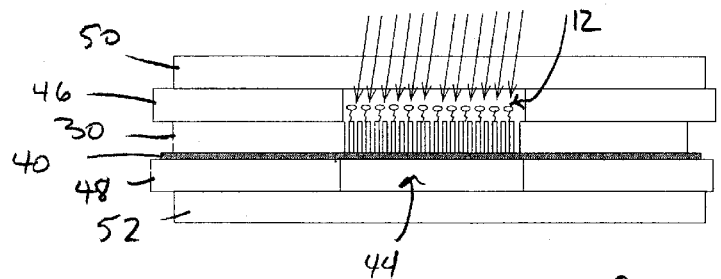
Figure 13A
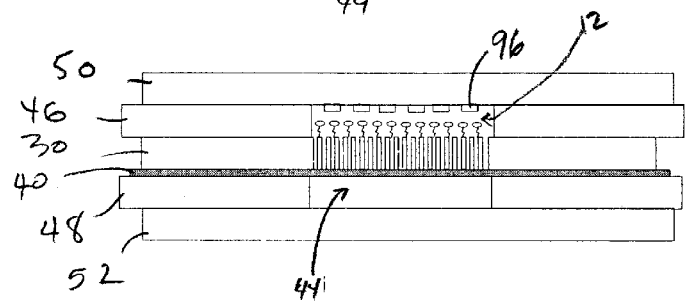
Figure 13B
Figure 14
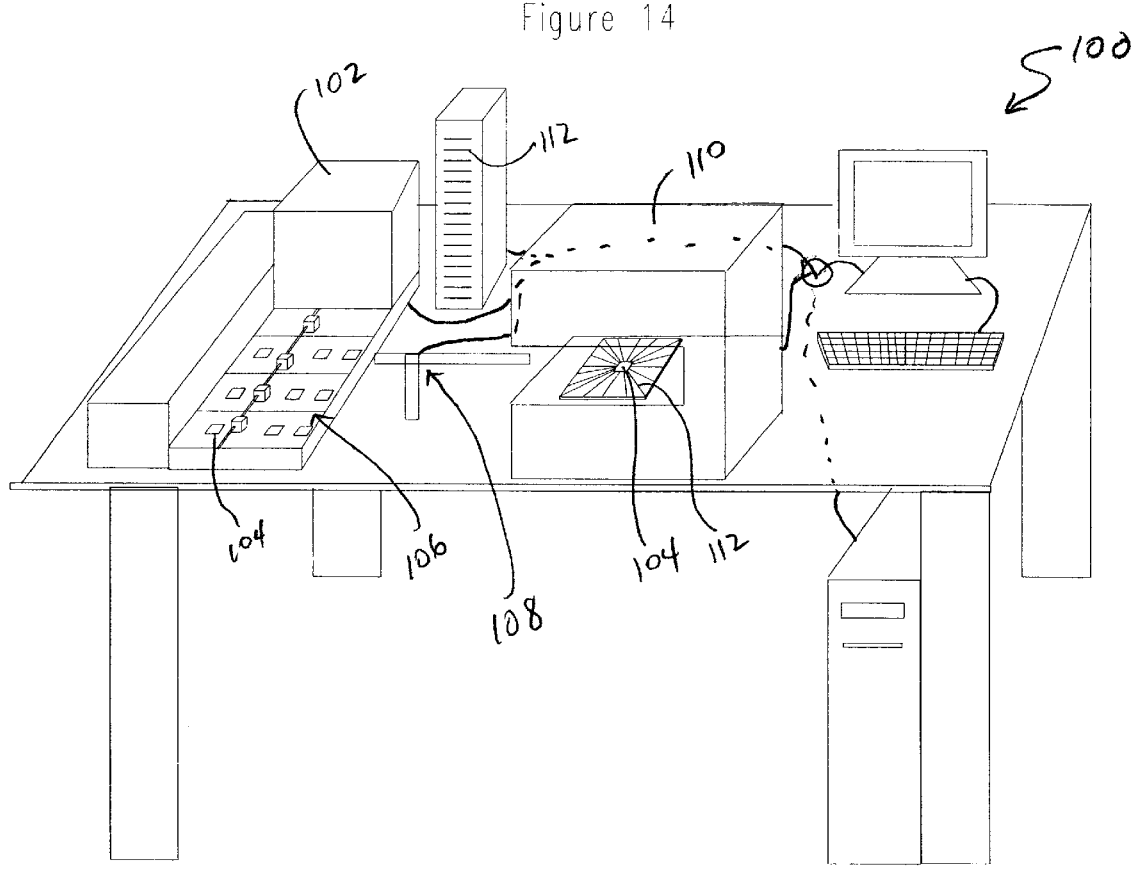

ARRAY-BASED MICROENVIRONMENT FOR CELL CULTURING, CELL MONITORING AND DRUG-TARGET VALIDATION

FIELD OF THE INVENTION

The present invention relates to the development of systems that permit the analysis, validation and rapid throughput of intracellular and extracellular targeting of cells and tissues cultured in a microenvironment.

BACKGROUND OF THE INVENTION

The ability to study complex or voluminous biological systems with a rigorous experimental model would be useful in a variety of medical industries. The pharmaceutical industry, for example, relies on High Throughput Screening (HTS) of libraries of chemical compounds to find drug candidates. HTS is a method where many discrete compounds are tested in parallel so that large numbers of test compounds are screened for biological activity simultaneously or nearly simultaneously.

The need in biotechnology for automation and miniaturization of components and reagent consumption is elevating interest in micro-fluidics, particularly the need for physically small pumps, valves, and mixing chambers. Microfabricated "lab-on-a-chip" instruments are emerging for conducting electrophoresis, radiography, protein sequencing, DNA diagnostics, and genotyping that require sample and reagent delivery systems capable of regulating volumes in the 10–1000 nanoliter range.

Miniature biosensors and drug delivery systems are other arenas requiring microfluidic pumps, valves, pipes, and vessels. Micromachined peristaltic pumps may be provided and arranged to deliver a reagent from a reservoir and a sample liquid specimen from a supply source through micromachined delivery channel sections to a reaction chamber. The reaction chamber may output to a detector.

SUMMARY OF THE INVENTION

The present invention provides methods and apparatus for cell culturing in a microenvironment. The environment allows cell culturing in an array format. The invention allows for either introducing cells via microfluidics or printing of cells directly on to the bottom plate which is attached to the controlled microenvironment. A variety of cells could be cultured in the various arrays. The various cells are cultivated with nutrient flow in and out of each culture well. The present invention combines Microfluidics with wafer bonding and attachment to obtain the 3-D microfluidic channel network.

The present invention is useful for analyzing and quantifying several molecular targets within a sample substance using an array having one or more cells, or small molecules applied on a thinfilm substrate which is attachable to the controlled microenvironment. The invention may be used with microarrays in microenvironment for diagnostics, drug discovery and screening analysis, gene expression analysis, cell sorting, microorganic monitoring, micropatterned cell culturing and microsynthesis. Various types of arrays are possible. The following are some of the examples.

One type of array is micropatterned co-cultures. Photolithography is used to pattern biomolecules on glass substrates to create micropattern of cultures of two or more distinct cell types, for example, patterns of hepatocytes and fibroblasts. In this arrangement, cell to cell interactions can be studied based on the specific cell to cell geometry pattern. This geometry pattern can be varied systematically on a glass substrate and this substrate can be attached to the rest of the chip structure for perfusion and analysis. Patterning of cells can also be done by microcontact printing, photobiochemistry and by using digital micromirrors.

The invention can be used in high throughput screening (HTS) strategies designed to identify potential pharmaceuticals from a library of chemical compounds. The devise will enable the investigator to control the precise application (concentration, time of delivery, and delivered volume) of multiple compounds into a microarray of chambers, each containing a parallel culture of viable cells, and simultaneously monitor the real-time effects of that application on various biological processes defined by the user.

The ability to deliver fluids into the culture environment through multiple channels further enables the user to employ both homogenous and heterogeneous assay protocols using the various fluorescent, calorimetric, and bioluminescent reporter systems currently available. Fluorescently labeled biomolecules such as proteins, phospholipids, nucleic acid probes, fluorescent tagged antibodies and synthetic fluorescent reagents with specific binding properties have long been used as reporter molecules to determine the location, amount and chemical environment of subcellular targets and biomolecules.

Such assays are routinely used to monitor the transcriptional activity of a genetic locus throughout the course of an experiment, protein-protein interactions, receptor-ligand interactions, enzymatic activity, basic cell processes such as DNA synthesis and cell division, transmembrane fluxes, pH fluctuations, synthesis of metabolites and countless other biological processes. Furthermore, the ability to transport and segregate viable cells into discrete micro-chambers will further enable the investigator to construct an array of different cell types and simultaneously evaluate the effects of a particular compound or set of compounds on a predefined biological process. For example, the ability of a putative drug to block cell proliferation may be tested on several types of tumor cell lines as well as normal cells at the same time.

Moreover, the device disclosed herein may be used to determine the pharmacokinetic properties of a particular drug on multiple cell types, each cultured in parallel. The invention is particularly suited for tissue engineering applications, which involve the growth and controlled differentiation of, e.g., stem cell lines. Such cells can be cultured in the micro-chambers and treated with a variety of compounds designed to induce differentiation into a particular cell type. Once the appropriate treatment regimen has been established, the device may even be used as a bioreactor to manufacture differentiated cells for therapeutic use.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 3A is a side view cross section of portion A of FIG. 1;

FIG. 3B is a side view cross section of portion B of FIG. 1;

FIG. 4A is a side view cross section of portion A of FIG. 1 for an alternative embodiment of the present invention;

FIG. 4B is a side view cross section of portion B of FIG. 1 for an alternative embodiment of the present invention;

FIG. 5 is a side view cross section of portion A of FIG. 1 for another alternative embodiment of the present invention;

FIG. 6 is a side view cross section of FIG. 1 for still another alternative embodiment of the present invention;

FIG. 7 is a side view cross section of FIG. 1 for a further alternative embodiment of the present invention;

FIG. 8 is a side view cross section of FIG. 1 for yet a further alternative embodiment of the present invention;

FIG. 9 is a top view of an array on a substrate of the present invention;

FIG. 10 is a side view cross section of FIG. 1 for yet another alternative embodiment of the present invention;

FIG. 11 is top view of a hydrophylic or hydrophobic array substrate of the present invention;

FIG. 12 is a side view cross section of a non-detachable embodiment of the present invention;

FIG. 13A is a side view cross section of a substrate of the present invention depicting temperature control with a digital micromirror;

FIG. 13B is a side view cross section of a substrate of the present invention depicting temperature control with a meandering electrode; and FIG. 14 is perspective schematic of an arrangement of a system of the present invention;

DETAILED DESCRIPTION OF THE INVENTION

Figure 2:
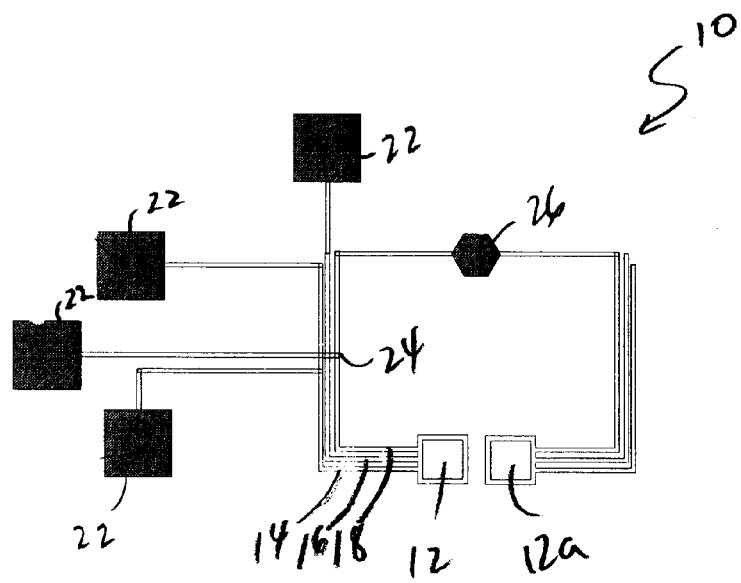
FIG. 2 is a top view schematic of microwells of the present invention connected on the same wafer or on a circuit board with microfluidic control elements such as valves, pumps, and sensors etc.

While the making and using of the various embodiments of the present invention are discussed in detail below, it should be appreciated that the present invention provides many applicable inventive concepts which can be embodied in a wide variety of specific contexts. The specific embodiments described herein are merely illustrative of specific ways to make and use the invention and do not delimit the scope of the invention nor the scope of the claims appended hereto.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used throughout the present specification one or more of the following abbreviations may be used: TF, transcription factor; ORF, open reading frame; kb, kilobase (pairs); UTR, untranslated region; kD, kilodalton; PCR, polymerase chain reaction; RT, reverse transcriptase.

The term "nucleotide sequence" and similar terms, with respect to nucleotides, refers to sequences that substantially correspond to any portion of a sequence identified herein. This term refer to synthetic as well as naturally-derived molecules and includes sequences that possess biologically, immunologically, experimentally, or otherwise functionally equivalent activity, for instance with respect to hybridization by nucleic acid segments, or the ability to encode all or portions of such activities. Naturally, these terms are meant to include information in such a sequence as specified by its linear order.

The term "amino acid sequence" and similar terms, with respect to amino acids, refers to peptides, polypeptides, proteins, fragments, fusions, derivatives and alterations thereof. These terms refer to synthetic as well as naturally-derived molecules and includes sequences that possess biologically, immunologically, experimentally, or otherwise functionally equivalent activities, for instance, segments of amino acids which possess immunological activity as an antigenic determinant. Naturally, these terms are meant to include information in such a sequence as specified by its linear order.

The term "homology" refers to the extent to which two nucleic acids are complementary. There may be partial or complete homology. A partially complementary sequence is one that at least partially inhibits a completely complementary sequence from hybridizing to a target nucleic acid and is referred to using the functional term "substantially homologous." The degree or extent of hybridization may be examined using a hybridization or other assay (such as a competitive PCR assay) and is meant, as will be known to those of skill in the art, to include specific interaction even at low stringency.

The inhibition of hybridization of the completely complementary sequence to the target sequence may also be examined using a hybridization assay involving a solid support (e.g., Southern or Northern blot, solution hybridization and the like) under conditions of low stringency. Low stringency conditions may be used to identify the binding of two sequences to one another while still being specific (i.e., selective). The absence of non-specific binding may be tested by the use of a second target that lacks even a partial degree of complementarity (e.g., less than about 30% identity). In the absence of non-specific binding, the probe will not hybridize to the second non-complementary target and the original interaction will be found to be selective.

Low stringency conditions are generally conditions equivalent to binding or hybridization at 42 degrees Centigrade in a solution consisting of 5×SSPE (43.8 g/l NaCl, 6.9 g/l $NaH_2PO_4$—$H_2O$ and 1.85 g/l EDTA, pH 7.4), 0.1% SDS, 5×Denhardt's reagent (50×Denhardt's contains per 500 ml: 5 g Ficoll (Type 400, Pharmacia), 5 g BSA (Fraction V; Sigma) and 100 micrograms/ml denatured salmon sperm DNA); followed by washing in a solution comprising 5×SSPE, 0.1% SDS at 42 degrees Centigrade when a probe of about 500 nucleotides in length is employed.

The art knows that numerous equivalent conditions may be employed to achieve low stringency conditions. Factors that affect the level of stringency include: the length and nature (DNA, RNA, base composition) of the probe and nature of the target (DNA, RNA, base composition, present in solution or immobilized, etc.) and the concentration of the salts and other components (e.g., formamide, dextran sulfate, polyethylene glycol). Likewise, the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, inclusion of formamide, etc.).

The term "gene" is used to refer to a functional protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated.

As used herein, the term "vector" is used in reference to nucleic acid molecules that transfer DNA segment(s) from one cell to another. The vector may be further defined as one designed to propagate a desired nucleotide sequences, or as an expression vector that includes a promoter operatively linked to the desired nucleotide sequence, or one designed to cause such a promoter to be introduced. The vector may exist in a state independent of the host cell chromosome, or may be integrated into the host cell chromosome.

The term "host cell" refers to cells that have been engineered to contain isolated nucleic acid segments, or altered segments, whether archeal, prokaryotic, or eukaryotic. Thus, engineered, or recombinant cells, are distinguishable from naturally occurring cells that do not contain recombinantly introduced genes through the hand of man.

The term "agonist" refers to a molecule that enhances either the strength or the time of an effect of stimulating a biological or biochemical effect and encompasses small molecules, proteins, nucleic acids, carbohydrates, lipids, or other compounds. The term "antagonist" refers to a molecule that decreases either the strength or the time of an effect of decreasing a biological or biochemical effect and encompasses small molecules, proteins, nucleic, acids, carbohydrates, lipids, or other compounds.

The term "altered", or "alterations" or "modified" with reference to nucleic acid or polypeptide sequences is meant to include changes such as insertions, deletions, substitutions, fusions with related or unrelated sequences, such as might occur by the hand of man, or those that may occur naturally such as polymorphisms, alleles and other structural types. Alterations encompass genomic DNA and RNA sequences that may differ with respect to their hybridization properties using a given hybridization probe. Alterations of polynucleotide sequences, or fragments thereof, include those that increase, decrease, or have no effect on functionality. Alterations of polypeptides refer to those that have been changed by recombinant DNA engineering, chemical, or biochemical modifications, such as amino acid derivatives or conjugates, or post-translational modifications.

A "substrate" may be made of silicon, gallium arsenide, silicon on insulator (SOI) structures, epitaxial formations, germanium, germanium silicon, polysilicon, amorphous silicon, and/or like substrate, semi-conductive or conductive. The substrate is typically made of single crystal silicon, and is usually lightly doped with boron, phosphorous or arsenic atoms.

"Moats" or open fluidic lines may be disposed within, e.g., a field oxide region or a polysilicon layer on a substrate. Moats are often constructed adjacent a polysilicon layer deposited on a substrate (when the substrate is silicon-based). Moat regions are generally formed by diffusion, and may have disposed therein a hydrophilic surface that permits or encourages fluid transfer through the moat. The moat may be covered to form a fluidic line. Alternatively, the moats may be used to provide conductive regions for accessing electrical connections that control, e.g., valves, pumps, fluid gates, sensors and the like on a substrate. One advantage realized by the present invention is that valves, pumps and even the chamber for cell growth may be addresses not unlike a source/drain in DRAM cells, in which the source drain may be common to one or more locations that are being addressed via fluid or electrically. A moat becomes a "fluidic line" when the moat is covered.

When addressing control elements on the surface of a substrate to control fluidic events electrically, electric routing lines may be disposed adjacent to the fluidic conduits. Generally, an insulating layer will cover electric routing lines. In this way, during manufacture, both the fluidic conduits and the electrical control connections may be formed or deposited using standard wafer processing techniques, such as: field growth, plasma deposition and photolithography. These techniques are combined, e.g., to form the fluid and electrical portions of the cell culturing system. The fluidic and electrical components will generally by electrically isolated by insulating layers, except where a sensor or other control device may be included at the surface of a fluidic line too e.g., regulate flow or take a biological or biochemical measurement.

High Throughput Screening

The most widely established HTS techniques use a 96-well microtitre chamber format. For use with the present invention, independent tests may be performed simultaneously on a single 6, 9, or 12 inch wafer that contains, e.g., 96 reaction chambers or wells. These chambers typically require assay volumes that range from 50 to 500 microliters. In addition to the wafers, many instruments, materials, pipettors, robotics, plate washers and plate readers are commercially available to fit the 96-well format to a wide range of homogeneous and heterogeneous assays.

Efforts to improve HTS have focused on miniaturization to make the microtiter wells smaller. Reduced well size increases the number of wells on each wafer to provide more samples for parallel testing. Miniaturization decreases the assay volumes, and decreases the cost of reagents per test. One can run more parallel tests with smaller assay volumes and simultaneously test more compounds to find drug candidates. Miniaturization has, for example, increased the microtiter-well number from 96 wells to a 384-well (96 times 4) format. See Comley et al., J. Biomol. Screening, vol. 2(3), pp. 171–78 (1997). Higher density formats have been reported, including a 9600-well format. Miniaturization, however, has inherent problems such as cost and complexity.

The problems of miniaturization relate directly to the components of a screening format. For example, the containers (tubes, wells, dimples, etc.) must be smaller. Also, one must be able to accurately dispense all of the necessary assay reagents into more and smaller wells (usually accomplished by liquid handling robots that simultaneously dispense the reagents into many wells). Finally, one must be able to detect the results of the assays in the high density array.

Given the requirements of parallelized independent assays, each component provides challenges and limits to how much miniaturization is feasible or cost effective. Indeed, a newer, smaller format may require a completely different method of dispensing reagents, or require a reading instrument that has the resolution, sensitivity and engineering that is compatible with the newer, miniaturized format. As the size of the well is reduced, the ability to fabricate the container array, to dispense reagents in smaller quantities, and to detect each test sample also becomes more difficult, time consuming, and costly. Moreover, a smaller sample size also increases the statistical variability from sample to sample because of the inherent inaccuracies in dispensing smaller volumes of reagents and in measuring weaker sample signals. Moreover, as sample size decreases beyond a certain point, factors like evaporation and surface tension add even greater cost and complexity to implementing miniaturized formats.

Nucleic Acid Hybridization

Another field of biology where miniaturization has become important is nucleic acid hybridization. The expression levels of various genes are indicative of many disease states and nucleic acid hybridization assays may be diagnostic of such pathogenic gene expression. Differences in the copy number of the genetic DNA or through changes in levels of transcription (e.g. through control of initiation, provision of RNA precursors, RNA processing, etc.)of particular genes are often characteristic of disease.

Losses and gains of genetic material, for example, play an important role in malignant transformation and progression. Changes in the expression of oncogenes or tumor suppressor genes may be diagnostic or predictive of such malignant transformation. Oncogenes are positive regulators of tumorgenesis. Tumor suppressor genes are negative regulators of tumorgenesis (Marshall, Cell, 64: 313–326 (1991); Weinberg, Science, 254: 1138–1146 (1991)).

An increase the number of genes coding for oncogene proteins or an increase in the level of expression of these oncogenes (e.g., in response to changes of the cell or environment), often result in unregulated cellular growth. Similarly, the loss of genetic material or a decrease in the level of expression of genes that code for tumor suppressors may lead to malignancy. For example, it has been shown that losses and gains of genetic material are associated with glioma progression (Mikkelson et al. J. Cellular Biochem. 46: 3–8 (1991)). Changes in the expression (transcription) levels of particular genes (e.g., oncogenes or tumor suppressors), are therefore well recognized indicators of the presence and growth of various cancers.

The cell cycle and cell development are also characterized by the variations in the transcription levels of particular genes. A viral infection, for example, is often characterized by elevated expression of genes of the particular virus. Outbreaks of many disease-causing viruses, such as Herpes simplex, Epstein-Barr virus infections (e.g. infectious mononucleosis), cytomegalovirus, Varicella-zoster virus infections, parvovirus infections, human papillomavirus infections and others, are characterized by elevated expression of genes present in the respective virus. An effective diagnostic of the disease state caused by the virus is to detect elevated expression levels of characteristic viral genes. Further, many viruses such as herpes simplex, enter quiescent states for periods of time only to break out in explosive periods of rapid replication. The detection of expression levels of characteristic viral genes allows diagnosis of such proliferative and infective activity of the virus.

Oligonucleotide probes have long been used to detect complementary nucleic acid sequences in a nucleic acid of interest (the "target", "test" or "experimental" nucleic acid) and have been used to detect expression of particular genes (e.g., a Northern Blot). In some assay formats, the oligonucleotide probe is immobilized or tethered, i.e., by covalent attachment, to a solid support, and arrays of oligonucleotide probes so immobilized on solid supports have been used to detect specific nucleic acid sequences in a target nucleic acid. See, e.g., PCT patent publication Nos. WO 89/10977 and 89/11548. The use of oligonucleotide probes has been proposed to sequence a target nucleic acid.

Methods for constructing, e.g., a cDNA microarray involve depositing or printing double stranded cDNA products onto glass slides coated with a substance such as poly-lysine, followed by ultraviolet (UV) cross-linking. Printing refers to any of a variety of means known to those of skill for immobilizing nucleic acid on a solid support in a pattern or array. U.S. Pat. No. 5,919,626, issued Jul. 6, 1997 to Shi, et al., for example, describes a variety of methods to immobilize nucleic acid on a solid support, including ink-jet printing.

The expression level of, for example, 10,000 or more independent samples deposited or created on a substrate may be analyzed by hybridization arrays that bind to cells, viruses or tissues. To deposit that many samples of a single slide, a microchemical spotting system may be used. Such systems are presently used at Stanford University, California, or from Synteni, U.S.A. Alternatively, other slide spotting systems may be built using array technologies such a photolithographic techniques and photodeprotection chemistry.

High density arrays of oligonucleotide (or other) probes are an emerging technology for research and potential clinical diagnostics. Arrays of up to 65,000 oligonucleotides, manufactured using photolithographic methods are now available commercially from Affymetrix/Hewlett Packard. The arrays are used for resequencing and expression studies via hybridization to the array. The array chips currently have feature sizes of approximately 20 microns.

Automated slide spotter systems in conjunction with a high-throughput reader analysis for gene expression determinations are commercially available from Genomic Solutions, Inc., Ann Arbor, Mich., such as the GeneTAC $G^3$ Robotic Workstation.

A slide spotter such as the GeneTAC $G^3$ Robotic Workstation from Genomic Solutions, Inc., Ann Arbor, Mich., uses solid pins with a "dip and print" technique using about nanoliter of sample for each feature on a slide may be used to spot an array of the present invention. Alternatively, a slide spotter may be constructed from, e.g., a Toshiba high precision/reproducibility pick and place robot with a multichannel spotting head. The Toshiba robot is programmable from a teach pendant or via PC computer. Different types of print heads may be used to pot slides, e.g., a pin spotter, a microvalve/capillary potter or a piezoelectric/capillary spotter. These rovide options of increasing accuracy, complexity and risk. An ultra clean environment is maintained using a HEPA filter to pressurize robot operating volume and proper clean room practices. Microwell plates are kept cool using a surface chiller to minimize evaporation.

Specifications for a slide spotter can include a spot volume of 500 picoliters to 10 nanoliters, a total volume deposited of 500 picoliters (if used with 40 slides this requires 20 nanoliters to 400 nanoliters of volume), and a total sample prime volume of 2 microliters. A drop size for use with slide spotting may be 90 picoliters (e.g., a piezo shooter system, 0.5–1.0 nanoliters for microvalve, or 1–10 nanoliters for pin tool). The system should provide a spot reproducibility of approximately >95%. Shoot times of 6 milliseconds (piezo) to 0.1 seconds (microvalve or pin tool)

may be used. Spot dimensions may be of up to about 100 microns on a slide size of, e.g., one inch×three inches. A post grid or orientation may be of 48×144 post, with a slide spot area of 0.75×2.25 inches (about 19 mm×57 mm). The distance between spots may be of about 0.19 mm/48 spots which totals 396 microns. The X-Y step size and reproducibility of a Toshiba robot is about 20.3 microns, which yields an X-Y step between spots of 396 microns/20.3 microns to give 19 spots. For example, a slide spotter a 384-well plate may be used, with up to about 18 384-well plates kept on a chilled plate to control evaporation. The samples "on deck" or queued in the plates may be of about 6,912. Slides on deck may be, e.g., forty, if six spotter pins/shooters are used per robot arm. Basic functions or steps per cycle can include: clean, aspirate, prime/verify shooter and spot.

Arrays may be fabricated by spotting cells. The in vitro manipulation, study and processing of individual cells is useful for the in vitro assaying of compounds for biological activity in such cells. Conventional biological assay systems such as flow cytometry and cell perfusion chambers, however, are typically operated with relatively large volumes from 1 to 100 ml of reagents or more. The present invention overcomes the disadvantages of techniques involving large volumes of reagents and cells is the inability to observe the effects on a particular cell before, during and after it comes into contact with a compound of interest. Moreover, statistical variations within a population of cells may limit the ability to resolve the effect of a compound on the cells.

Recently small disposable devices have been developed for handling biological samples and for conducting in vitro experiments on a controlled basis. For example, microchips have been used to electrophoretically separate mixtures of amino acids. Integrated capillary electrophoresis device where electrophoresis is used to separate mixtures of amino acids have been described. The manipulation of a single cell by its electrophoretic mobility has been shown in a capillary. Microchips have been designed to evaluate sperm function, principally motility, for in vitro fertilization.

Analysis of the effects of compounds on cell function demands careful handling of compounds that are often limited in both quantity and concentration. The ability to observe the effect of the compounds on individual cells in a device potentially suitable for a high level of multiplexing makes miniaturized analysis very attractive. Furthermore, the present invention permits the observation of effects by compounds on non-adherent cells.

The microfluidic systems embodied in a microchip disclosed herein use small volumes, providing cost saving advantages for work involving expensive reagents, especially compounds made for new drug screening and of course would reduce the amount of compound required.

The ability to sort cell responses into classes and analyze each class separately reduces the apparent statistical variation seen when large number of cells are evaluated. Single cell studies also allow the progression of events within a single cell to be evaluated, in contrast to flow cytometry where a progression of events is studied over an ensemble of cells. Statistical variations within an ensemble can limit the ability to resolve a particular effect, whereas working with individual cells will maximize resolution and signal to noise for a given event.

Microarrays of Cells

Methods have been described for making uniform micropatterned arrays of cells for other applications, for example photochemical resist photolithograpy. Mrksich and Whitesides, Ann. Rev. Biophys. Biomol. Struct. 25:55–78, 1996. According to this photoresist method, a glass plate is uniformly coated with a photoresist and a photo mask is placed over the photoresist coating to define the "array"or pattern desired. Upon exposure to light, the photoresist in the unmasked areas is removed.

The entire photolithographically defined surface is uniformly coated with a hydrophobic substance such as an organosilane that binds both to the areas of exposed glass and the areas covered with the photoresist. The photoresist is then stripped from the glass surface, exposing an array of spots of exposed glass. The glass plate then is washed with an organosilane having terminal hydrophilic groups or chemically reactable groups such as amino groups. The hydrophobic organosilane binds to the spots of exposed glass with the resulting glass plate having an array of hydrophilic or reactable spots (located in the areas of the original photoresist) across a hydrophobic surface.

The array of spots of hydrophilic groups provides a substrate for non-specific and non-covalent binding of certain cells, including those of neuronal origin. Kleinfeld et al., J. Neurosci. 8:4098–4120, 1988. Reactive ion etching has been similarly used on the surface of silicon wafers to produce surfaces patterned with two different types of texture (Craighead et al., Appl. Phys. Lett. 37:653, 1980; Craighead et al., J. Vac. Sci. Technol. 20:316, 1982; Suh et al. Proc. SPIE 382:199, 1983).

In another method based on specific yet non-covalent interactions, photoresist stamping is used to produce a gold surface coated with protein adsorptive alkanethiol. (Singhvi et al., Science 264:696–698, 1994). The bare gold surface is then coated with polyethylene-terminated alkanethiols that resist protein adsorption. After exposure of the entire surface to laminin, a cell binding protein found in the extracellular matrix, living hepatocytes attach uniformly to, and grow upon, the laminin coated islands (Singhvi et al. 1994).

One such method of cell adhesion involves strong, but non-covalent, metal chelation has been used to coat gold surfaces with patterns of specific proteins (Sigal et al., Anal. Chem. 68:490–497, 1996). In this case, the gold surface is patterned with alkanethiols terminated with nitriloacetic acid. Bare regions of gold are coated with tri(ethyleneglycol) to reduce protein adsorption. After adding $Ni^{2+}$, the specific adsorption of five histidine-tagged proteins is found to be kinetically stable. More specific uniform cell-binding can be achieved by chemically crosslinking specific molecules, such as proteins, to reactable sites on the patterned substrate. Aplin and Hughes, Analyt. Biochem. 113:144–148, 1981.

Another method of substrate patterning optically creates an array of reactable spots. A glass plate is washed with an organosilane that absorbs to the glass to coat the glass. The organosilane coating is irradiated by deep UV light through an optical mask or by using a micromirror array that defines a pattern of an array. The irradiation cleaves the Si—C bond to form a reactive Si radical. Reaction with water causes the Si radicals to form polar silanol groups. The polar silanol groups constitute spots on the array and are further modified to couple other reactable molecules to the spots, as disclosed in U.S. Pat. No. 5,324,591, relevant portions incorporated herein by reference.

For example, a silane containing a biologically functional group such as a free amino moiety may be reacted with the silanol groups. The free amino groups are used as sites of covalent attachment for biomolecules such as proteins, nucleic acids, carbohydrates, and lipids. The non-patterned covalent attachment of a lectin, known to interact with the surface of cells, to a glass substrate through reactive amino groups has been demonstrated (Aplin & Hughes, 1981). The optical method of forming a uniform array of cells on a support requires fewer steps and is faster than the photoresist method, (i.e., only two steps), but it requires the use of high intensity ultraviolet light from an expensive light source.

Microfluidics

Efficient delivery of solutions to an array of cells attached to a solid substrate, is facilitated by a system of microfluidics. Methods and apparatus have been described for the precise handling of small liquid samples for ink delivery (U.S. Pat. No. 5,233,369; U.S. Pat. No. 5,486,855; U.S. Pat. No. 5,502,467), biosample aspiration (U.S. Patent No. 4,982,739), reagent storage and delivery (U.S. Pat. No. 5,031,797), and partitioned microelectronic and fluidic device array for clinical diagnostics and chemical synthesis (U.S. Pat. No. 5,585,069), all relevant portions incorporated herein by reference.

In addition, methods and apparatus have been described for the formation of microchannels in solid substrates that can be used to direct small liquid samples along the surface (U.S. Pat. No. 5,571,410; U.S. Pat. No. 5,500,071; U.S. Pat. No. 4,344,816), relevant portions incorporated herein by reference).

Optical Reading of Cell Physiology

Performing a high throughput screen on many thousands of compounds with cells requires parallel handling and processing of many compounds and assay component reagents. Standard high throughput combinatorial chemistry screens use homogeneous mixtures of compounds and biological reagents along with some indicator compound, loaded into arrays of wells in standard microtiter plates with 96 or 384 wells (Kahl, et al., J. Biomol. Scr. 2:33–40, 1997). The signal measured from each well, either fluorescence emission, optical density, or radioactivity, integrates the signal from all the material in the well giving an overall population average of all the molecules in the well. This type of assay is commonly referred to as a homogeneous assay.

Science Applications International Corporation (SAIC) 130 Fifth Avenue, Seattle, Wash. 98109 describes an imaging plate reader, (U.S. Pat. No. 5,581,487, herein incorporated by reference). This system uses a CCD detector (charge-coupled optical detector) to image the whole area of a 96 well plate. The image is analyzed to calculate the total fluorescence per well for homogeneous assays.

Molecular Devices, Inc. describes a system (FLIPRM) which uses low angle laser scanning illumination and a mask to selectively excite fluorescence within approximately 200 microns of the bottoms of the wells in standard 96 well plates in order to reduce background when imaging cell monolayers.

Schroeder and Neagle describe a system that uses a CCD camera to image the whole area of the plate bottom. Schroeder and Neagle, J. Biomol. Scr. 1:75–80, 1996. Although this system measures signals originating from a cell monolayer at the bottom of the well, the signal measured is averaged over the area of the well and is therefore still considered a homogeneous measurement, since it is an average response of a population of cells. The image is analyzed to calculate the total fluorescence per well for cell-based homogeneous assays.

Proffitt, et al., describes a semi-automated fluorescence digital imaging system for quantifying relative cell numbers in situ, where the cells have been pretreated with fluorescein diacetate (FDA) (Cytometry 24:204–213, 1996). The system uses a variety of tissue culture plate formats, particularly 96-well microtiter plates. The system consists of an epifluorescence inverted microscope with a motorized stage, video camera, image intensifier, and a microcomputer with a PC-Vision digitizer. Turbo Pascal software controls the stage and scans the plate taking multiple images per well. The software calculates total fluorescence per well, provides for daily calibration, and configures for a variety of tissue culture plate formats. Thresholding of digital images and reagents that fluoresce only when taken up by living cells are used to reduce background fluorescence without removing excess fluorescent reagent.

A variety of methods have been developed to image fluorescent cells with a microscope and extract information about the spatial distribution and temporal changes occurring in these cells. Many of these methods and their applications are described by Taylor, et al., Am. Scientist 80:322–335, 1992. These methods have been designed and optimized for the preparation of small numbers of specimens a for high spatial and temporal resolution imaging measurements of distribution, amount and biochemical environment of the fluorescent reporter molecules in the cells.

Dyes, fluorescent reagents and genetic engineering of cells to produce fluorescent proteins, such as modified green fluorescent protein (GFP) as a reporter molecule, are useful methods for the detection and imaging of cells. Wang et al., Methods in Cell Biology, New York, Alan R. Liss, 29:1–12, 1989. The green fluorescent protein (GFP) of the jellyfish Aequorea victoria has an excitation maximum at 395 nm, an emission maximum at 510 nm and does not require an exogenous factor. Uses of GEP for the study of gene expression and protein localization are discussed in Chalfie, et al., Science 263:802–805, 1994. Some properties of wild-type GFP are disclosed by Morise, et al., Biochemistry 13:2656–2662, 1974, and Ward, et al., Photochem. Photobiol. 31:611–615, 1980. Rizzuto, et al., discusses the use of wild-type GFP as a tool for visualizing subcellular organelles in cells. Nature 358:325–327, 1992. Kaether and Gerdes (FEBS Letters 369:267–271, 1995) report the visualization of protein transport along the secretory pathway using wild-type GFP.

The expression of GFP in plant cells is discussed by Hu and Cheng (FEBS Letters 369:331–334, 1995), while GFP expression in Drosophila embryos is described by Davis et al. (Dev. Biology 170:726–729, 1995). U. S. Pat. No. 5,491,084, relevant portions incorporated herein by reference, discloses expression of GFP from Aequorea victoria in cells as a reporter molecule fused to another protein of interest. PCT/DK96/00052, relevant portions incorporated herein by reference, relates to methods of detecting biologically active substances affecting intracellular processes by using a GFP construct having a protein kinase activation site. Numerous references are related to GFP proteins in biological systems. For example, PCT/US95/10165 incorporated by reference herein, describes a system for isolating cells of interest utilizing the expression of a GFP like protein. PCT/GB96/00481 incorporated by reference herein, describes the expression of GFP in plants. PCT/US95/01425 incorporated by reference herein, describes modified GFP protein expressed in transformed organisms to detect mutagenesis. Mutants of GFP have been prepared and used in several biological systems. (Hasselhoff et al., Proc. Natl. Acad. Sci. 94:2122–2127, 1997; Brejc et al., Proc. Natl. Acad. Sci. 94:2306–2311, 1997; Cheng et al., Nature Biotech. 14:606–609, 1996; Heim and Tsien, Curr.

Biol. 6:178–192, 1996; Ehrig et al., FEBS Letters 367:163–166, 1995). All of these methods may be used with the present invention.

Methods describing assays and compositions for detecting and evaluating the intracellular transduction of an extracellular signal using recombinant cells that express cell surface receptors and contain reporter gene constructs that include transcriptional regulatory elements that are responsive to the activity of cell surface receptors are disclosed in U.S. Pat. No. 5,436,128 and U.S. Pat. No. 5,401,629, both of which are incorporated by reference herein.

The ArrayScanυ System, as developed by BioDx, Inc. (U.S. application Ser. No. 08/810983), e.g., is an optical system for determining the distribution, environment, or activity of luminescently labeled reporter molecules in cells for the purpose of screening large numbers of compounds for specific biological activity. The ArrayScan™ System involves providing cells containing luminescent reporter molecules in a uniform array of locations and scanning numerous cells in each location with a fluorescence microscope, converting the optical information into digital data, and used the digital data to determine the distribution, environment or activity of the luminescently labeled reporter molecules in the cells.

The uniform array of locations used presently are the industry standard 96 well or 384 well microtiter plates. The ArrayScan™ System includes apparatus and computerized method for processing, displaying and storing the data, thus augmenting drug discovery by providing high content cell-based screening in a large microtiter plate format.

The standard microtiter plate format, i.e., the 96 well microtiter plate, has 6 mm diameter wells on a 9 mm pitch. Higher density plates, such as 384 well plates, reduce both the well size and well pitch (for example to 3 mm and 4.5 mm), packing more wells in the same format.

Reducing the well size and the array size not only improves the speed and efficiency of scanning for high-content screening, but also allows high throughput screening to be carried out on the same cell array by reading the whole area of the array at lower spatial resolution. Thus, high throughput primary screens can be directly coupled with high-content secondary screens on the same platform. In effect, the high-content screen becomes a high throughput screen. There is also a dramatic savings in the volumes of costly reagents and drug candidates used in each screening protocol. Furthermore, the delivery of cells to the "wells" is based on specific binding, thus high precision droplets need not be delivered to specific locations. As used herein, the term "wells" does not refer to any depth but merely the location of a cell binding site on the base.

Microfluidic Substrates

A simple form of a microfluidic structure has two base layers between which an elastic spacing material, which is firmly attached to at least one of the base layers and forms a geometric micro structure defining the desired liquid flow system, e.g., one or more cavities or a labyrinth-like channel. To provide the liquid flow system, the spacing layer may be recessed through a part or the whole thickness thereof. The spacing layer forms the side walls and one of the top and bottom walls of each cavity or channel, one of the base layers forming the other of the top and bottom walls, whereas in another case the base layers form the top and bottom walls and the spacing layer forms the side walls. The spacing layer may be elastic to provide adequate sealing thereof to the respective base layer(s) is obtained.

Another microfluidic embodiment includes of a "multi story" sandwich structure having two or more spacing layers separated by base layers. The liquid flow systems in adjacent spacing layers communicate by apertures or bores in the intermediate base layers. Thus, complex flow channel systems may be formed. Piling several base layer/spacing layer assemblies on top of each other is one way to form such a multi story structure.

The base layers should generally be form-stable, including both non-elastic materials and moderately elastomeric materials. The purpose of the base layers is to support the spacing layer and to form part of the channel or cavity walls, as well as to maintain and ensure the dimensions of the structure in the XY-plane thereof. The XY-plane is that of the base layer plane extension, and Z is the direction perpendicular thereto. Form-stable, therefore, refers to a material that will give only small and well-defined dimensional changes under conditions dictated by the particular application.

The base layer surface should have a good surface smoothness to ensure efficient sealing under moderate pressures. A suitable surface may be obtained, for example, by the base layer being stiff or by using a flexible film placed on a planar and possibly elastic surface. Suitable materials for the base layer, which may be in plate, sheet, foil or film form, include: silicon, glass, metal or plastic, such as polyester, polyethylene terephthalate, e.g. Mylar, fluoroplastic, e.g. Hostaflon. The above mentioned apertures in the base layer, useful for, e.g., sandwich applications, may be accomplished by high precision techniques such as laser drilling or numerically controlled precision machinery.

As mentioned above the purpose of the spacing layer is to build up the side walls of the channels or cavities and provide for the desired elasticity in the Z-direction, i.e., perpendicularly to the plane extension. The material should thus be elastic, i.e., preferably be a rubber or an elastomer. An example of a suitable type of material is silicone rubber, EPDM rubber and Hostaflon.

Depending upon the method used for the manufacture of the base layer/spacing layer assembly, which will be described in more detail below, the spacing layer material should also have satisfactory properties as a molding material, such as low viscosity and form shrinkage, a suitable curing or hardening principle, e.g., UV-light or other radiation, temperature, etc. as well as a suitable hardness to provide for efficient sealing. The above properties makes it possible to transfer and multiply with great accuracy the exact geometry from precision-made molds or dies to cheap polymeric materials. Such high precision molds or dies may, for example, advantageously be fabricated by etching in single crystal materials.

The elastic or resilient properties of the spacing layer or layers permit a very good seal between base and spacing layers, or between adjacent spacing layers, to be obtained. The spacing layer (when stabilized) may also have surface properties providing for suitable surface characteristics when joined to a base layer and defining a cavity or channel therewith, e.g., hydrophobic-hydrophobic interaction for applications involving aqueous solutions.

Concerning the basic structure of the invention including two base layers and an intermediate spacing layer, it is readily realized, however, that there are materials that will satisfy at the same time the requirements on both the base layer and the spacing layer. The spacing layer and one or both of the base layers may then be made of the same material. In such a case the spacing layer and one base layer may also be integral. The multi-story structure may, of course, also be made up from such integral base layer/spacing layer units. An example of a material that may be used in this respect is Hostaflon.

In one embodiment, the spacing layer does not fill the whole space enclosed by the two base layers, but only to the extent for sufficient wall thicknesses of the channels or cavities defined thereby. For example, in a winding channel the spacing layer material defining it will exhibit the same winding geometry but with a wider cross-section. In this way, a smaller sealing area is obtained, thereby requiring a smaller total sealing force to be applied for a given surface pressure.

The elasticity of the spacing layer(s) may also be used to give the structure the function of a pump or valve by varying the force acting in the Z-direction, i.e., normally to the base and spacing layer planes. The force required to compress the structure to obtain such a pumping action will also be smaller the shorter the spacing layer extension.

The required recessing of the spacing layer is accomplished by forming the spacing layer against a planar mold, e.g. a sheet or plate, which has a molding surface provided with a relief pattern being the negative of the desired geometric structure to be exhibited by the spacing layer. Such a mold may, for instance, be produced by etching, surface coating, laser processing, electrochemical etching, mechanical processing, or combinations thereof, of a substrate of, for instance, silicon, quartz, ceramic, metal or plastic material, e.g., PMMA or Teflon™. The mold used for forming the spacing layer may very well be a replica of an originally manufactured master mold produced therefrom by casting or molding.

One method of producing such a mold involves etching. The material of choice is then a single crystalline material, including silicon or quartz, or various group III/V materials, including gallium arsenide, i.e., a material which has such a structure/composition that a well-defined surface will be produced by chemical processing in gas or liquid phase, and which has such mechanical/thermal properties that it will withstand the pressures and temperatures required by such forming process. One such material is a single crystalline silicon.

The etching of a desired relief pattern on the surface may be effected, e.g., by providing the substrate with an etch stopper layer (usually by oxidation), coating with a photosensitive layer (photoresist), exposing the surface through a mask defining the desired relief pattern, and developing the exposed areas to remove the photoresist therefrom. The bared etch stopper layer is then opened in those areas, removing the remaining photoresist mask, and finally etching the bared substrate surface areas to the desired depth.

The molding of the spacing layer may be performed in various ways. For instance, in one embodiment the spacing layer is formed by compression molding, involving impression, or coining or embossing, of the spacing layer material. In this case, the spacing layer material, optionally attached to or integral with a base layer, is applied against the mold surface, and the assembly is pressed together by an external force. In case the material is thermoplastic, increasing the temperature thereof lowers the viscosity and the spacing layer relief pattern formed is then made permanent or stabilized by lowering the temperature. Other ways of stabilizing the spacing layer include cross-linking thereof, e.g., by UV-radiation, a catalyst, heat, etc. The spacing layer material may be a thin layer of a cross-linkable liquid, such as a silicone rubber, coated on the surface of the base layer.

In another embodiment, the spacing layer is formed by an injection molding. The base layer is applied against the mold surface, and the base layer and the mold are pressed together by an external force. A cross-linkable liquid, e.g., a silicone rubber, is then pressed into the mold cavity formed, whereupon it is cross-linked by appropriate cross-linking means, such as UV-light. Alternatively, a thermoplastic polymer melt might be injected to form the spacing layer when stabilized by cooling.

When the hardening or stabilization of the spacing layer is completed, the base layer/spacing layer assembly is removed from the mold. In order to facilitate the release of the formed spacing layer from the mold, the latter may be treated with a release agent prior to the molding operation, e.g., a fluorotenside in liquid phase or a fluoropolymer in gaseous phase.

After removal from the mold, the second base layer may be applied to the spacing layer to complete the desired cavity or channel system. Optionally, the second base layer may be covalently or otherwise bound to the spacing layer by suitable.

To achieve optimum sealing between the spacing and base layers, the assembly is placed in a clamp between planar faced clamps capable of exerting a compressive force on the assembly. Other clamping methods may also be used to make the assembly perform the pumping action.

For electrophoresis, the second base layer may be provided with two electrical contacts, e.g., gold strips, at each end. In such a case, this second base layer may be made reusable.

Microfluidic structures may, of course, advantageously also be designed for other microfluidic purposes than electrophoresis. Among those are, e.g., capillary chromatography, micro-reaction cavity procedures, miniaturized liquid communication units, biosensor flow cells, cell culture, and so forth. Reaction cavities constructed in accordance with the invention may, for example, be used for various forms of solid phase synthesis, such as peptide or oligonucleotide synthesis, PCR, DNA-solid phase sequencing reactions, just to mention a few.

Adhesive and Encapsulation

The use of adhesive layers and encapsulation of the microchambers may also be used in conjunction with the present invention. Example, a liquid thermo-setting plastic such as liquid epoxy or a polyimide may be used as an adhesive. Epoxies are used because of their toughness, processibility, rigidity, chemical resistance, low shrinkage and adhesive properties. Epoxies are also used because they can adhere to a wide variety of substrates, organic and inorganic. While there are many different epoxy resins, most commonly epoxies are formed by reacting diglycidyl esters of Bisphenol-A with epichlorolhydrin. In many cases, bromine is reacted into the phenol ring section of the molecule to improve flame retardance. Multifunctional epoxies may also be used with the present invention, and are characterized by having more than two epoxide rings per monomer.

The basic epoxy resin may be cured or crosslinked by adding a coreactant or catalyst. Many different compounds can react with either the epoxide ring or the hydroxyl group of the epoxy ring such as aliphatic amines, aromatic amines, and anhydrides, or catalysts such as piperidine or boron trifluoride ethylamine. The advantage of using an aliphatic amine as a curing agent for epoxies is that curing occurs at room temperature or temperatures slightly above room temperature, the curing is fast, it is resistant to low heat and is a high exotherm. Examples of aliphatic amines that may be used to cure epoxies include diethylene triamine or dicyandiamide, for example.

Alternatively, an aromatic amine may be used to cure the epoxy, the advantages being a long pot life, elevated curing temperatures and higher heat resistance. Samples of aromatic amines that may be used with the present invention include metaphenylene diamine or diamino diphenyl sulfone. Alternatively, anhydrides may be used, such as hexahydrophthalic anhydride. Anhydrides may be selected because they are safer, have a very long pot life, can be cured at an elevated temperature and have very high heat resistance.

Another advantage of epoxy based adhesives is that they can be made with any viscosity, from liquid to solid, and can be flexible or rigid, based on the types of mineral fills or fibers that are used to fill the epoxy. Another advantage of epoxies is that they can be combined with glass containing fabrics to produce laminated printed circuit boards, such as FR-4.

Alternatively, a liquid adhesive used with the present invention can be a polyimide polymer. Polyimide polymers may be used as an adhesive due to their heat resistance at cryogenic temperatures and their radiation resistance. Polyimides also have favorable electric properties and low outgassing, making them extremely useful in the extreme environment of space and at high temperature. Typically, copolymers used to polymerize polyimides are amideimide, imide phenolics, bismaleimide, epoxy imides and polyester imides.

Alternatively, the adhesive layer may be a liquid epoxy such as X-43-5000, available from Shi-Etsu Chemicals, Ltd., or polyimides such as G7631, -G8320 or Hitachi HM122u. The bonding process generally involves attaching the subsatrate 30 on a printed circuit board at a temperature above room temperature and allowing the epoxy or polyimide liquid adhesive to cure.

An important parameter of polymeric materials is the glass transition temperature, $T_g$. The $T_g$ is the temperature at which long-range co-operativity between polymer chains becomes sufficient to allow the material to deform in response to an external force. For use with the present invention a temperature of about 215 and 250° C. during processing is used to cure the thermosetting adhesive for use in the process of the present invention.

Printed circuit boards for use with the invention may be constructed from a material such as FR-4 which is available from, for example, Motorola Inc., U.S.A. FR-4 is an epoxy resin reinforced with a woven glass cloth. In selecting the material for printed circuit board, one skilled in the art will recognize that four parameters should be considered, namely, thickness, dielectric constant, glass transition temperature and the coefficient of thermal expansion.

Thickness is dependant on the number of layers required and the amount of reinforcement used in a given layer. The reinforcing glass cloth can range in thickness from 2 mil per sheet (type 106) to about 8 mil per sheet (type 7628). Dielectric constant is determined by a combination of the resin used and the thickness and type of reinforcement used. Standard FR-4 has a dielectric constant of about 4.5. This constant can be reduced to about 3 by replacing the epoxy resin with a cyanate ester resin. The greater the thickness, however, the greater the problems associated with thickness control, rough surfaces, excessive drill reflection and poor resin refill.

The temperature at which a resin changes from a glass-like state into a "rubbery" state is generally designated as $T_g$.

Standard FR-4 is made with a bifunctionally polymerizing epoxy that has a $T_g$ of about 110° C. Higher $T_g$ temperatures, such as 125–150° C. may be withstood by using a tetrafunctional epoxy. For higher $T_g$ values, in the range of 150° to 200° C. a cyanate ester:epoxy blend can be used. Additionally, polyimides provide for printed circuit boards having a $T_g$ above 250° C.

The coefficient of thermal expansion for FR-4 is about 16 ppm/C. A difference in the coefficient of thermal expansion between the printed circuit board made from FR-4 and the substrate 30 may lead to failure of the integrated circuit/microchamber package during, not only the assembly of the integrated circuit/microchamber package, but also during the use of integrated circuit/microchamber package.

Microfluid Control Elements

Microvalves

Microfluidic valves may include an electrostatically controlled flap valve positioned in a fluidic, or an electromagnetic valve embedded in a moat of fluidic line or conduit. Printed electrical control lines electrically connected to the microvalves may be used to provide electrical signals that open or close the valves. In addition to electrostatic or electromagnetic valves, other conventional valves known to those skilled in the art may be used, including but not limited to flap valves, movable membrane valves, slide valves, hinge or butterfly valves, piezoelectric, electrorheological, thermoexpansive, or shape memory alloy valves, bimorph based thermal valves, rotary, or even simple pressure actuated spring valves.

As will be appreciated, microactuators such as valves may be constructed with a variety of machining or micromachining techniques, including those associated with conventional integrated circuit or printed circuit board fabrication. For example, chemical etching, electron beam lithography, photolithography, laser ablation, or other standard integrated circuit processing technologies may be used to define necessary valve apertures. Alternatively, injection molding, high precision numerically controlled machines, or stereolithography may be employed for valve construction. Materials used in construction may include plastics, metals, glasses, or ceramics. In one possible embodiment, plastics, epoxies, glass, silicon, polysilicon, silicon nitride, silicon oxide, oxynitride, plastics or metals such as electroplated copper or aluminum, or any other available material suitable for lithographic processing may be used to define the necessary microactuator, valve, valve housing, valve structures, or conduits.

Electrodes may be any conductive metal or polymer, while movable components may be constructed from electroplated copper, plastic films, aluminum coated mylar, plated nickel, or polyimide sandwiched aluminum. Large arrays of the microactuators having one or more movable components may be constructed, with small scale arrays having tens or even hundreds of thousands of individual microactuators distributed throughout a dielectric substrate in accordance with the present invention.

To precisely control fluid flow through conduits, electromagnetic valves constructed in part using conventional printed batch processing techniques are particularly suitable. For example, an actively addressable electromagnetic valve may be constructed in part from movable components and structures formed on a substrate according to the present invention. The substrate may be drilled, etched, mold formed or otherwise modified to define a microchamber having an inlet for inward flow and an outlet for outward flow. A compressively stressed membrane constructed from substantially uniform permalloy or other magnetically susceptible material may be positioned in the chamber. The membrane is stressed to normally close the valve by blocking the outlet.

To open the valve requires electrically addressing (with, e.g., a row address line and a column address line) an electrical lead such as a copper planar coil formed on a dielectric layer of the substrate. In conjunction with a permalloy layer, this creates sufficient electromagnetic force to pull the membrane to an open position, opening the valve and allowing fluid into the chamber to escape through the outlet. When the current is reduced, the mechanically biased membrane springs back into blocking position, closing the valve.

An alternative embodiment of an electromagnetic valve relies on an imposed mechanical bistability for a membrane to permit passive matrix addressing. In contrast to the membrane discussed above, biased to be normally closed, the membrane of this embodiment is bistable, being stable both in a closed position, and in an opened position. The valve is very similar to the previous valve, differing only the addition of a secondary copper planar coil (with row and column address lines) formed on a dielectric layer of the substrate, along with a secondary permalloy layer.

In operation, electrically addressing the copper planar coil creates sufficient electromagnetic force to pull the membrane to an open position, opening the valve and allowing fluid in the chamber to escape through the outlet. When the voltage is reduced, the mechanically biased membrane is left in one of its two mechanically stable positions, so it remains in that open position. To close the valve, the row and column address lines may be transiently electrically addressed, resulting in sufficient electromagnetic force to pull the membrane to its original blocking position, closing the valve and preventing fluid in the chamber from escaping through the outlet.

Another bistable valve embodiment of an electromagnetic valve is stable both in a closed position, and in an opened position. The bistable valve differs from the previous uniform permalloy membranes by use of permalloy patterning to create a poled magnetic layer and magnetic field line patterns.

In operation, voltage addressing of the copper planar coil causes current flow in the coils to create sufficient electromagnetic force to pull the membrane to an open position, opening the valve and allowing fluid in the chamber to escape through the outlet. When the current is reduced, the mechanically biased membrane is left in one of its two mechanically stable positions, so it remains in that open position. To close the valve, the row and column address lines may be transiently electrically addressed to reverse current direction, resulting in sufficient electromagnetic force to push the magnetically-poled membrane to its original blocking position, closing the valve and preventing fluid in the chamber from escaping through the outlet.

Yet another single coiled electromagnetic valve has a bistable membrane stable both in a closed position, and in an opened position, and only requires a single coil for bistable operation, with reversal of current direction in the coil causing the membrane to move back and forth between the open and closed position. In contrast to valves described above, however, the membrane of the valve supports a planar coil rather than the planar copper coil being supported by a dielectric.

In operation, electrically addressing the copper lanar coil causes current flow in the coils to create sufficient electromagnetic force to pull the membrane toward a poled permalloy region, opening the valve and allowing fluid in the chamber to escape through the outlet. When the current is reduced, the mechanically biased membrane is left in one of its two mechanically stable positions, so it remains in that open position. To close the valve, voltage address lines may be transiently electrically addressed to reverse current direction, resulting in sufficient electromagnetic force to push the magnetically poled membrane to its original blocking position, closing the valve and preventing fluid in the chamber from escaping through the outlet. As compared to the magnetically poled embodiment, the valve described has faster operation due to the lower inductance and lower mass of the planar coil relative the transiently created permalloy magnetic circuit.

In addition to electromagnetic valves, other valve structures may of course be used in the present invention. For example, a simple electrostatic flap valve formed using a bonded dual laminate substrate may be batch constructed by appropriate modification of conventional printed circuit board construction techniques. Such a valve is formed by laminating a first board to a second board. The first board has a drilled out air outlet conduit and supports an anchor and flap, both generally formed from etched copper or other conductor, optionally coated with an insulative layer such as parylene. The second board has an electrical lead actively addressable by row and address lines to apply a predetermined threshold voltage sufficient to hold the flap closed against fluid pressure applied through a drilled out inlet. Since the flap valve is normally open under applied fluid pressure, to open the valve merely requires one of the addressing lines to reduce applied voltage to the electrodes, allowing the flap to move away from the surround electrodes and causing fluid to jet through outlet. As will be appreciated, various modifications of this valve scheme are contemplated, including but not limited to rearranging the flap to maintain a normally closed, rather than normally open position.

Other valve structures may be formed by using a number of printed circuit board/microelectromechanical construction techniques. For example, passively addressable electrostatic flap valves and flap valve arrays may be constructed by soldering, gluing, using photo-patternable glues or laminates, electroforming fabrication techniques or any other conventional attachment techniques to form a mechanically bistable flap or flaps with flap anchors embeddable in a substrate. The flap covers a drilled out hole, and may be moved between an open and closed position only when both electrodes are addressed, with voltage addressing of a single electrode being insufficient to move the flap. If additional bistability for either flap designs is needed, provision of additional latch or "catch"electrodes that permit maintenance of a small constant voltage to hold a flap in position until application of much great switching voltage is also contemplated.

Micropumps

Micropumps, such as a micro-peristaltic pump, are useful to impel fluid movement in the microconduits of the present invention. For example, a pump channel may be etched into a substrate, lined with electrically conductive strips whose top surfaces are covered with electrically insulating material. The strips are separated from each other by electrically insulating barriers formed, e.g., at a right angle to the channel. The channel is then covered by an electrically conductive flexible membrane.

With no voltage applied, the membrane is linear in cross-section and lies over the channel. By applying a suitable voltage between the membrane and each of the conductive strips in succession, the membrane may be electrostatically pulled into the channel at successive positions along the length of the channel, thereby creating a peristaltic pumping action.

The characteristics and performance of such electrostatic actuated peristaltic pumps are principally dependent on the properties of the flexible membrane, which may exhibit an elasticity of about 30%. For low differential pressures and moderate temperatures a graphite impregnated polyurethane membrane material of thickness 5 micrometers is satisfactory. In vacuum applications, surface metallization of polyurethane membranes is necessary to reduce porosity. Higher voltages, such as 100 volts, are required to generate the electrostatic forces necessary to overcome the larger differential pressures, and high progression rates (500 m/sec) are required to pump nonviscous gases (vacuum pressures).

One embodiment includes a push-pull dual cavity of a microperistaltic pump, where two silicon substrates are placed together with a single membrane sandwiched between them. The membrane may again be graphite impregnated polyurethane. Between the membrane and each substrate are positioned respective conductive strip layers and respective insulating layers. Each substrate further has a linear conductor pit and a bond metal trench located adjacent one another and running parallel to a channel. While the thickness of the insulation layer must be of submicron dimensions to ensure high electrostatic forces on the membrane, the channels may be of millimeter dimensions.

A conductive strip layer often includes a number of actuator strip elements that begin at the top edge of the channel and traverse down the channel and up the channel to its opposite edge. Thus, the substrate top surface curves down on either side to form a walled channel having a rounded bottom portion such that no sharp edges are involved. The actuator strips are rectangular conductor elements lying parallel to one another, transversely to the channel and laid out down the length of the channel. They may be, for example, 0.1 millimeter in width such that a group of 200 strips occupies about 20 millimeters. The space between the elements is filled with insulation provided by an insulating layer to provide interstrip insulation that insulates each actuator element from the next element. Thinner lead elements travel away from each actuator element to a respective conductive pad that provides a wire bond pad for establishing electrical connection to a shift register or other electronic component. The actuator strips, leads, and pads may be formed by etching a single deposited conductive metal layer such as a gold layer.

Each conductor pit may have a conductor channel formed of conductive metal that establishes electrical connection to the membrane. The membrane has complementary upper and lower lips on respective ends that fit into and mate with a respective conductor channel to both establish electrical connection to the membrane and position and hold the membrane in place when the two substrates are bonded together and hermetically sealed with the assistance of bond metal placed in the bond metal trenches between the substrates and the insulation layers. A ledge is further formed on each substrate parallel to the channel in order to provide for membrane thickness and permit some squeezing to hold the membrane in position.

Micromachining techniques have evolved from the microelectronics industry. Both the additive processes of thin film deposition or vapor deposition and the subtractive processes of chemical or plasma etching are appropriate for the manufacture of both the channels and pump. The bulk etching of channels in silicon, quartz, or other suitable substrate, whether semiconductor, metallic, or otherwise, and its fusing to a mirror image wafer is one technique of creating a microperistaltic pump. Surface micromachining may also be deployed where a patterned sacrificial profile of the channel is created over which the actuator and insulation materials are deposited.

Isotropic etching techniques may be employed in an embodiment of the micropump to create a smooth, contoured concave channel. Once this channel and other grooves and ledges have been created, a metal layer of a few hundred Angstroms in thickness is vapor or sputter deposited evenly over the whole top surface of substrate. An even layer of photoresist is then applied and a photo mask is thereafter used to define the etch barriers to form the metal actuator strips, leads, pads, and conductive membrane connection channels. The comparatively large depth of field required for submicron definition of the actuator elements in the channel may require special care.

Following the etching and removal of the photoresist, a vapor epitaxial deposit of a micron of silicon dioxide, or like insulation material, is required to form the insulation layers. The insulation layers provide the insulation between the actuator strips themselves, the insulation between the actuator strips and the membrane, and the insulation between the strips and the bond metal to be placed in the bond metal trenches.

After annealing the material to consolidate the insulation layer, another photoresist coating is applied and then another photo mask in order to define the membrane connection channel and insulation profile, e.g., to expose the conductive strip connection pads. The final wafer processing step involves the vapor or sputter deposition of a column of interwafer bond metal in the bond metal trenches, for example, using a shadow mask. The pump die shells or substrates are then cut from their wafer, the flexible membrane placed between two shells, and the assembly clamped together and placed in an oven until the bond metal melts, pulls the two dies together, and fuses the two dies together to form a solid structure hermetically sealed down both sides by the bond metal. A typical bond metal is a mixture of gold and germanium.

Where the membrane is clamped, it is in intimate contact with the thin insulation layer of both shells. When a voltage is applied between an actuator element and the membrane, an electrostatic attraction force, proportional to the square of the applied voltage and the inverse square of the insulation thickness (<1 micron), pulls the membrane down. The membrane rolls down the surface of the insulation, due to the fact that the greatest attractive forces are generated where distances from conductive strips are the smallest (i.e. insulation thickness). Conversely, when a voltage is applied to the strip in the upper shell, the membrane rolls up its channel surface.

When a neighboring conducting strip is energized the membrane rolls forward and down across the activated elements. The membrane is initially drawn up onto the upper channel surface and advanced along the channel, then the membrane is released for several periods before the membrane is drawn down into the lower channel and then rolls down the lower channel surface. Thus, a membrane "wall" is placed across the composite channel. By connecting the actuator elements up to the outputs of a shift register leads and pads, a clocked bit stream of "1s" or "0s" apply a voltage or no voltage with respect to the membrane, respectively, to the actuator elements along the channel in a sequential manner. The actuation progression provides a miniature peristaltic pump.

In the case of a dual channeled pump, dual shift registers may be used to provide interlaced and interlocked bit streams such that a membrane wall is advanced down channel. By alternate inversions of the bit streams sequences, multiple membrane "bubbles" will move down the channel, pushing the entrapped fluid in front of each membrane "wall" and pulling the fluid behind each membrane "wall".

The pump may be valveless and impervious to gas bubble entrapment. It also does not require priming and may tolerate the adherence of small foreign articles (small compared with cavity dimensions) on channel or membrane surfaces. The pump may also be self-purging by pushing everything before the membrane with its rolling motion across the channel surface.

Such pumps may deliver and measure minuscule volumes of "incompressible" liquids and at precisely determined times or time intervals, for example, by actuating the membrane at times recorded in the memory of a programmed digital processor or computer. The precision with which volumes may be measured (or delivered) by the disclosed microperistaltic pump is that associated with a single stepped advance of an actuator strip. The product of the channel cross-section and actuator pitch thus defines this minimum volume. For example, a relatively large channel, by micromachining standards, with a cross-section of 0.5 mm$^2$ and an actuator pitch of 0.1 mm has a minimum volume displacement of 50 nanoliters.

In continuous flow microreaction chambers, separate pumps may be used for each reagent and respectively run at clocking rates that are proportional to the required concentration ratios. In batch mode operation, providing sufficient clock pulses to deliver the necessary number of minimum volume displacements may meter specific volumes of reagents. When the pump is operated in the static or intermittent mode the "across channel" membrane functions as a valve. If reaction cells input ports are directly coupled to pumps the membrane "valves" may isolate the chamber against appreciable back pressure and for an indefinite period between successive deliveries of metered volumes of reagent.

If an electrostatic peristaltic pump will only function with fluids that are electrically non-conductive, magnetic renditions might be considered for electrically conductive fluids. Electrically conductive fluids are more complex, require significantly greater amounts of power and function over a more restrictive temperature range.

Micropumps have a number of advantages. At micron dimensions, small voltages create high electric fields over small distances that, in turn, are capable of generating substantial electrostatic forces. Electrostatic actuators consume no power (fractions of mW at high frequencies) and function from absolute zero to the eutectic melting temperatures of interwafer bonding materials.

Figure 1:
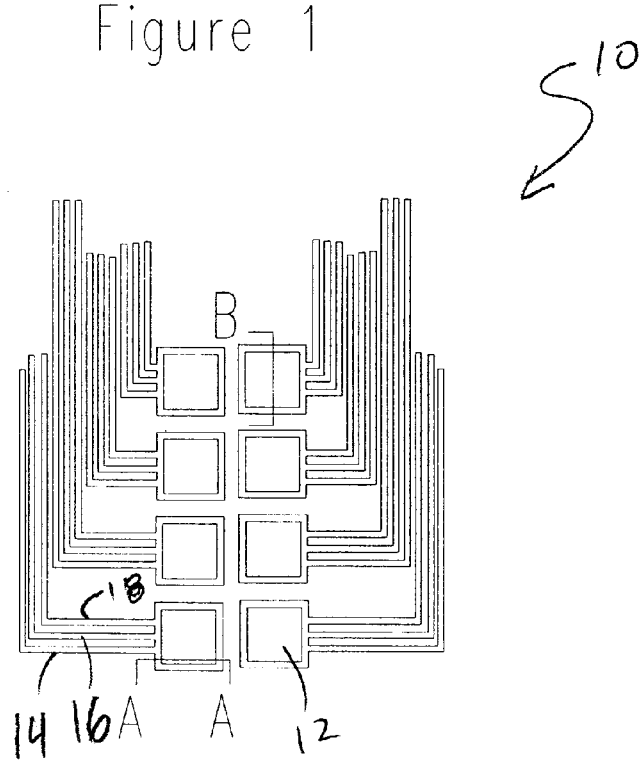
FIG. 1 is a top view schematic showing the array based cell culturing micro chambers of the present invention.

FIG. 1 shows an array 10 of cell culturing micro chambers 12 of the present invention. The chambers 12 have multiple fluid lines 14, 16 and 18. The fluid lines 14, 16 and 18 may serve as one or more fluid inlets, outlets and even a sampling portal. The fluid lines 14, 16, 18 may be used for bringing the sample (e.g., viruses, cells or tissues), in the chamber 12 nutrients, assay reagents, buffer solution, washing solution, etc. into the chamber 12. The outlets 16 serve to take, e.g., waste products out of the chamber 12 on a real-time and continuous basis. A third liquid routing line 18 may also be connected to bring more nutrients to the cell chamber or even as an alternative waste line. The liquid routing line 18 may also serve as a sampling portal for measuring metabolic activity of the sample in the chamber 12. If the sample is a cell line, e.g., the chamber 12 depicted may have an opening, e.g., a top opening, that permits access to the chamber 12 and that may be used to load the cells or other reagents from the top of the chamber, not unlike a micro titer plate.

Each of the one or more microwells or chambers 12 may be in contact with one or more fluidic lines 14, 16, 18. Traditional semiconductor processing techniques are used for silicon and glass including various wafer bonding techniques that are known to the one skilled in the art. Injection molding, hot embossing and other circuit board techniques with various plastic bonding techniques may be used to seal the various fluidic conduits. Examples of materials that may be used to create the microwells and conduits, in addition to silicon wafer materials include polyimide, polycarbonate, PMMA, nylon, teflon, PVDF and other polymers to prepare the substrates.

FIG. 2 is another top view of the chambers 12 of the present invention in which the chambers 12 are connected on the same wafer or on a circuit board with microfluidic control elements such as valves, pumps, and sensors etc. FIG. 2 provides an overview of the electrical connections that may be made to and from a chamber 12. Various microfluidic control elements 22 are depicted. These microfluidic control elements 22 may be used to define the control, in real-time, of the fluid inside the conduits 14, 16 and 18 that are connected to the arrayed chambers 12, and which help define the input and output of the fluid that enters and exits the chambers 12. The microfluidic control elements 22 may be valves 24 or pumps 26.

The chambers 12 may also be interconnected between each other for the purpose of taking, e.g., the excreted products from one cell line in one chamber 12, into the second chambers 12a with different cell lines present.

The various components are either integrally manufactured on a single wafer or batch assembled. Batch assembly gives flexibility with respect to combining elements processed by various process sequences. This flexibility is gained at a higher cost of assembly. Integrating all the processes on a single wafer gives low cost but is limited to a particular process sequence.

FIG. 3A shows a side view of one chamber 12 that has been formed on a substrate 30. A cell line 32 is depicted growing on top of a patterned substrate with controlled porosity or through-holes 34. The gap 36 between the through holes 34 is determined and controlled for the cells 32 to grow either only on the surface 38 or both on the surface 38 and in the through-holes 34.

In one embodiment, a membrane 40 (e.g., a nanoporous membrane) is attached to the bottom 42 of the patterned substrate 30. The purpose of the membrane 40 is to control, e.g., the size (e.g., molecular weight) and perhaps even the charge of fluids that are exchanged between a fluid in the chamber 12 and an opening 44 that serves and an outlet for a fluid that is used to exchange nutrients, gas, etc. between the chamber 12 and a fluid in the opening 44. The membrane 40 may, for example, separate fluids on one side and oxygen and nutrients, sample reagents, or carbon dioxide on the other side. In the embodiments depicted in FIGS. 3A and 3B, fluid in opening 44 may be common to all the chambers 12 in a multiarray system or may be specialized conduits that individually connect to each chamber 12.

In both FIGS. 3A and 3B, the sides of the chamber 12 and opening 44 may be formed from a variety of materials. For example, layers 46 and 48 may be grown from, or etched into, the substrate 30. Alternatively, layer 46 and 48 may be a printed circuit board (PCB) that contains electrical leads, conduits, vias, contacts, pads, etc., for control or detection of events within the chamber 12. A number of materials may be deposited on the substrate 30 to form the chamber, including materials deposited through chemicalvapor deposition or even synthetic materials that are printed, formed, molded, cut-out, etc. to form the one or more chambers 12.

As will be known to those of skill in the art of cellular biology, the selection of materials for creating the chamber 12 will generally be compatible with the biological sample that is placed in the chamber 12. Cellular attachment to the substrate 30, for example, may be encouraged or discouraged depending on the charge, if any, placed in the surface 38 of the chamber 12. As cell surfaces are generally negatively charged, a positive charge on the substrate (either inherent, injected, projected, deposited, etc.), will generally encourage cell adhesion.

FIG. 3B shows another embodiment of the microculture environment of the present invention in which more than one aopening 44 is routed underneath the membrane 40. By having one or more fluidic openings 44 different compositions may be removed or added to the chamber 12 through the different openings 44. One or more covers 50 and 52 may be affixed to the layers 46 and 48, respectively, in a permanent or semi-permanent manner. The covers 50, 52 may be synthetic or silicon based.

The covers 50 and/or 52 may even be a printed circuit board (PCB), as described hereinabove. When the covers 50 and/or 52 are a PCB, wiring leads, conduits, vias, pads, etc., may be integrated into the PCB to permit connection of the electrically controlling elements integral with or adjacent to the substrate 30 with outside connections. In fact, the substrate 30 may contain pads that are wire bonded, solder bonded or even directly connected to pads on the PCB for external connections, if required. The PCB may even be made of components that are light transparent or translucent for the use of light in, e.g., detection of events within the chamber 12.

In operation, the fluids that traverse the fluid lines or conduits (e.g., opening 44) may be drawn to and from the chamber 12 by gravitational or capillary forces. Capillary forces can draw fluids from, e.g., larger channels to smaller channels. Generally, capillary forces are largely controlled by the minimum cross-sectional dimension of a channel. For example, capillary forces can wick a fluid from a channel having a width of 100 micrometers and a depth of 20 micrometers into a contiguous channel having a width of 100 micrometers and a depth of 10 micrometers. In the absence of a microfluidic pump, simple gravitational or capillary forces may optionally be relied on to draw fluid through fluid channels, such as opening 44, into microfluidic channels within or adjacent to a substrate 30. Therefore, microfluidic channels that have a smaller cross-sectional dimension than the smallest cross-sectional dimension of the through-hole ports may be used to drive fluid flow.

Additional or alternative mechanisms are also available for injecting fluid through vias into the microfluidic channels or openings 44 in or adjacent to the substrate 30, including electrokinetics, differential pneumatic pressure, and the like. For example, simple liquid displacement may be used, under the control of, e.g. a pump or valve, to provide for fluid flow from an area of high liquid volume to one of lower liquid volume.

Alternatively, the present invention provides for the addition of electrical conducting routing lines that can provide an electrical current, potential, or charge to a valve and/or pump between a microfluidic opening 44 and a fluid within the opening at specific locations along the fluid line to inject or pump the fluid into the channel. For example, an electrical power source may be coupled to a waste fluid reservoir valve that controls the flow of fluid through a liquid line attached to the reservoir under the control of the reservoir valve.

As used therein, the term "valve" encompasses a structure within a microfluid substrate that allows access fluid control in microfluidic channels. The term "reservoir" encompasses ports and other structures that are formed in or adjacent to the substrate and which accommodate a significantly greater volume of fluid than the microfluidic channels. Other transportation mechanisms may be used to facilitate transfer of the fluids within fluid lines, such as through-holes or vias.

Useful substrate materials include glass, quartz and silicon, as well as polymeric substrates, e.g., plastics. In the case of polymeric substrates, the substrate materials may be rigid, semi-rigid, or non-rigid, opaque, semi-opaque or transparent, depending upon the use for which they are intended. Devices that include an optical or visual detection element, will generally be fabricated, at least in part, from transparent materials to allow, or at least facilitate that detection. As will be important for some of the embodiments of the present invention in which non-invasive detection procedures are used, transparent windows of, e.g., glass or quartz, may be incorporated into the device for these types of detection elements.

Polymeric materials for use with the present invention may include: linear or branched backbones, and may be crosslinked or non-crosslinked. Examples of particularly polymeric materials include: e.g., polymethylmethacrylate (PMMA) polydimethylsiloxanes (PDMS), polyurethane, polyvinylchloride (PVC), polystyrene, polysulfone, polycarbonate, and the like.

As will be apparent to those of skill in the art, specific minimum cross-sectional dimensions for fluidic lines provided by capillary force will depend on the wettability of the material bordering the port, the fluid to be retained therein, the distance between the channel and the bottom of the substrate if the fluidic via has a vertical orientation, and the like. For example, vias in many plastic materials will be smaller than similar vias in glass substrates, due to the higher wettability of glass.

Vias may be drilled through a substrate with a circular cross-section, the cross-section of the through-hole port typically having a diameter of between about 0.1 mm and 5 mm, and ideally having a diameter within the range of from about 0.5 mm to 2 mm. Such holes may be drilled using "air abrasion", that is, an erosion process that is similar to a precisely directed sandblast of the substrate material. Other methods include ultrasonic drilling or laser photoablation may be used to provide quite small ports through the substrate. In some embodiments, small carbide drill bits may mechanically drill through the substrate to provide vias having small enough cross-sectional dimensions to induce the desired capillary forces. Vias may also be formed during the substrate molding or embossing processes, particularly when the substrates are made of polymeric materials.

Turning now to FIGS. 4A and 4B, alternative arrangements are depicted in which the samples cells are grown directly on the surface 38, which may be, e.g., a chemically treated surface 38. The chemically treated surface 60 may be treated by doping the substrate 30 prior to, during, or following wafer processing. Alternatively, the surface 60 may be chemically modified with one or more compounds that promote or inhibit cellular adhesion, depending on the cell line, tissue and the like that will be grown on the surface 60. As with the chambers 12 depicted in FIGS. 3A and 3B, single and multiple fluidic conduits 44 are shown that may be used to bring fluids to and from the chamber 12. FIG. 4B shows the additional feature of stacking fluidic lines 44 and electrically conducting lines 54 disposed in an insulating layer 56.

FIG. 5 shows multiple chambers 12 in which two or more cells (32 and 32a) are co-cultured with multiple cell lines. Examples of situations in which such co-culture may be advantageous include the use of irradiated or other feeder layers for stem cell growth, antigen presentation assays and the like. In situations in which the user may want to increase the surface area on which to grow cells, beads may be included in the chamber 12 that will provide for increased surface for cell adhesion.

FIG. 6 shows a disconnectable chamber arrangement,j where the top head 70 contains the inlet fluidic 72 and the array platform 72 includes one or more chambers 12 of the platform 72 for the cell line 32 and the fluidic outlets 44. A gasket 74 allows for a seal that prevents liquid leaks.

FIGS. 7 and 8 show different locations for the gasket 74 in the embodiment having a top head 70. The specific arrangement where both the fluid inlets and outlets are on the top head 70 and the platform 72 may be included with any substrate chemically arrayed with a cell adhesion layer for use with certain cell lines grown in chambers 12. The multiple layer configuration permits increased flexibility when the chambers 12 arranged in an array fashion.

FIG. 9 shows a top view of an array 80 on a substrate 30. The substrate 30 may be directly attached to the top head 70 for fluidic processing. The chambers 12 may be, e.g., patterned by photolithographic techniques on the bottom plate. For example, hepatocytes may be arranged in a geometrical pattern as described on page 39 of reference (Sangeeta Bhatia, Microfabrication in Tissue Engineering and Bioartificial Organs, Kluwer Academic publishers, 1999). For example, Fibroblasts may be seeded around the hepatocytes giving an artificially cultured arrangement mimicking the liver tissue. The substrate 30 may then be accessed directly after a cell-drug interaction study in which artificially arranged cells are studied.

FIG. 10 shows an alternative arrangement in which the microculture chambers of the present invention are combined with digital micromirror technology to create the chambers 12. In one example, the digital micromirrors are used to create hydrophyllic and hydrophobic surfaces on the substrate 30 in which the surface 38 of the substrate 30 is differentially (location) and chemically modified to enhance or permit cell adhesion at specific locations on the substrate 30.

As shown in FIGS. 10 and 11, uniform cell-binding locations 90 may be disposed or created on the substrate by chemically modifying cell-repelling modifications 92 on the substrate with photosensitive chemistry using light 94 at selected locations using a micromirror array. The micromirror array may be used to selectively add or delete photochemically sensitive bonds on compounds deposited, built or etched onto the substrate 30 surface 38. Designs or patterns on the substrate 30 may be achieved by chemically crosslinking specific molecules, such as proteins, to reactable sites on the patterned substrates.

For example, the substrate may be washed with an organosilane that absorbs to e.g., the substrate. The organosilane coating is irradiated by deep UV light that is reflected by a digital micromirror that defines a pattern of the array 90. The irradiation cleaves the Si—C bond to form a reactive Si radical. Reaction with water causes the Si radicals to form polar silanol groups. The polar silanol groups constitute spots on the array and are further modified to couple other reactable molecules to the A spots. A silane containing a biologically functional group such as a free amino moiety can be reacted with the silanol groups. For example, antibodies, Lectins and other proteins may be reacted with the amino group, which is known to interact with the surface of cells. The pattern may be dictated, for example, by creating a pattern for the non-specific cell arrangement on the substrate by the digital micromirror.

FIG. 12 demonstrates an additional use for digital micromirror arrays. The surface chemistry modification is not easy with non-detachable devices such as in FIGS. 3, 4 and 5. One example where modifications after fabrication are necessary include circumstances when the chemical modifications in non-detachable devices have to occur after device fabrication, for example, where the surface can not be modified prior to the device fabrication because the high temperature process of bonding the wafer would destroy the modified chemical surface. Therefore, the chemical modification has to occur after device fabrication.

In the method and device illustrated in FIG. 12, the used takes advantage of photochemistry to generate the arrayed chemistry. The technique is similar to the above description where, photomasks or preferably digital micromirror device are used to illuminate the substrate in an array fashion. The required chemicals and washing cycles are carried out by delivering the right chemicals into each microwell via the fluidic lines 44 or opening. Using micromirror array directed chemical modification of the substrate 30 may be used to form arrays within arrays. In operation, a pattern may be formed into the chamber 12 during wafer processing and later reprocessed or features added, in situ, using optically sensitive chemistry. Generally, the top 50 will be made of a partially or completely light translucent substance.

FIGS. 13A and 13B depict alternative methods for measuring events that occur within a chamber 12. In FIG. 13A, the micromirror array is used to excite fluorescent compounds injected into the chamber 12 that may interact with, and cause luminescence of, one or more fluorescent compounds in the chamber 12. One advantage of using a micromirror array for causing exitation of selective portions of the array is that portions may be irradiated differentially, which is particularly important for situations in which bleaching of the exitation site may occur.

FIG. 13B demonstrates the integration of electrical conduits or pads 96 into the chamber 12, which may be used to, e.g., control the electrical potential of fluids within the chamber 12. Alternatively, the electrical pads 96 may be used to pulse cells on the surface of the chamber with electricity, e.g., when electroporating cells. The electrical conduits or pads 96 may be connected to a centralized controller that is connected to a computer (not depicted).

To make electrical connections from electrically driven, controlled, sensing and other like devices integral or disposed on the substrate 30 several alternatives will be known to those of skill in the art, such as, wire bonding or the use of electrically connecting pads.

Additionally, cell culture temperature may be achieved and maintained by either using a digital micromirror to reflect laser light pattern into the microwells or to use a meandering electrode in the microwell.

FIG. 14 the overall arrangement of the system 100 includes, e.g., a liquid dispensing printer 102 for printing the fluid droplets on to the substrate or chip 104. Various printer heads are used for various reagents including the cell dispensing. The printer 102 may include reagent cartridges with various compartments for various reagents and a liquid dispenser head. The liquid dispenser head may be of any type of bulk or surface micromachined silicon device, PZT, needle injectors, pins etc. Nanoliter volumes can be dispensed precisely using this technique.

In operation, dispensing may be conducted using a multihead printer 102 or arrayer. The printer 102 has the dispensing head on top and a multi track x-y stage 106 on the bottom on which the chips 104 are loaded by a robot 108 into the various tracks, depending on which reagent or fluid is needed to be dispensed onto the chip 104.

Optical as well as electrochemical sensing is possible due to the adaptation of wafer prober station 110.

Examples of probes include: fluorescent or chemiluminescent detection and wafer 112 or chip 104 probing electrical contacts 112 are made by conventional means employed in semiconductor manufacturing or by MEMS based actuators.

The current design lends itself to easy disposal of liquid handling devices. Disposable components serves to limit cross contamination between the various components and would lead to a very clean liquid handling. The entire setup may be required to be under, e.g., a class 1,000–100,000 clean room air.

While the structures are here illustrated as having, e.g., constant diameters these and other feature sizes may decrease near one or both surfaces. Vias may be drilled through the entire substrate in one operation, or may alternatively be drilled independently through separate upper and lower portions of the substrate prior to further processing. The cross-section of the vias may not be the same through the upper and lower portions, and should be tolerant of some mismatch between the size and location of the openings in the substrate. A wide variety of alternative valves and pumps also be used, with the diameter ranges given above generally defining the minimum cross-sectional dimension. The channel network may provide for the sensing the pH, oxygen level, and temperature as the microenvironment control parameters. The cell growth can be monitored through the bottom of the glass chip and florescent assays can be carried out.

Although the invention has been described in connection with specific embodiments, it should be understood that the invention as claimed should not be unduly limited to such specific embodiments. Modifications and variations of the described compositions and methods of the invention will be apparent to those skilled in the art without departing from the scope and spirit of the invention. Indeed, various modifications of the described compositions and modes of carrying out the invention which are obvious to those skilled in molecular biology or related arts are intended to be within the scope of the following claims.

What is claimed is:

1. An apparatus, comprising:
   one or more microchambers;
   wherein the one or more of the microchambers are adapted to contain cells;
   one or more fluid conduits in fluid communication with the microchamber;
   one or more valves adapted to regulate the flow of a fluid to the one or more microchambers;
   one or more reagent reservoirs in fluid communication with the one or more fluid conduits, wherein the valve regulates the flow of fluids between the one or more microchambers and the one or more reagent reservoirs adapted to exchange nutrients, oxygen and remove excretions; and
   the one or more microchambers adapted to contain cells is substantially planar.

2. The apparatus of claim 1, further comprising at least one pump in fluid communication with the fluid conduit.

3. The apparatus of claim 2, further comprising a valve controller adapted to control the at least one pump.

4. The apparatus of claim 2, further comprising a pump controller.

5. The apparatus of claim 1, further comprising one or more sensors in fluid communication with the one or more microchambers, the one or more fluid conduits or the one or more reagent reservoirs.

6. The apparatus of claim 1, integrated on a substrate.

7. The apparatus of claim 6, wherein the substrate is integral with at least one of a following element from a group consisting of:
   the fluid conduit;
   the microchamber; and
   the reagent reservoir.

8. The apparatus of claim 1, further comprising an array of arrays coupled to the substrate.

9. The apparatus of claim 1, further comprising an array associated with the one or more microchambers.

10. The apparatus of claim 1, wherein the one or more microchambers form a part of an array.

11. The apparatus of claim 1, further comprising encapsulation of the one or more microchambers, one or more fluid conduits and one or more fluid reservoirs.

12. The apparatus of claim 1, wherein the one or more microchambers comprise a cell adherent surface.

13. The apparatus of claim 1, wherein the microchambers form a 4-, 6-, 12-, 48-, 96- or 384-microchamber array.

14. The apparatus of claim 1, further comprising a diode array in fluid communication with the microchamber or the reagent reservoir.

15. The apparatus of claim 1, further comprising a micromirror array adjacent to and facing the microchamber or the reagent reservoir.

16. The apparatus of claim 15, wherein the microchamber further comprises a chemically treated substrate integral with the microchamber suitable for culturing cells wherein the micromirror array directs a light source onto the chemically treated substrate to produce a patterned array of photochemically treated substrate in the microchamber.

17. The apparatus of claim 16, wherein the light source is integral to the apparatus.

18. The apparatus of claim 16, wherein the light source comprises a laser.

19. The apparatus of claim 16, wherein the light source comprises ultraviolet light.

20. The apparatus of claim 16, wherein the substrate is treated with an organosilane.

21. The apparatus of claim 20, wherein the organosilane further comprises a biologically functional group.

22. The apparatus of claim 21, wherein the biologically functional group comprises a free amino moiety.

23. The apparatus of claim 22, wherein lectin is reacted with the free amino moiety to provide a cell adherent substrate.

24. The apparatus of claim 16, wherein a microprocessor controls the micromirror direction of the light source onto the substrate.

25. The apparatus of claim 16, wherein the micromirrors are positioned to direct light into the microchamber to regulate the temperature of the microchamber.

26. The apparatus of claim 16, wherein the patterned array is produced in a covered microwell.

27. A method for producing a patterned.array of cultured cells in the cell culture apparatus of claim 16, the method comprising the steps of:

treating the substrate with one or more photosensitive chemicals;

directing light of a selected wavelength at the micromirrors whereby the micromirrors re-direct the light onto the treated substrate in an array pattern to produce a substrate having photochemically treated portions wherein the photochemically treated portions of the substrate form a patterned array of photochemically treated substrate; and adhering cells to the substrate whereby the cells adhere to the photochemically treated portions of the substrate to produce a patterned array of cultured cells.

28. The method of claim 27, wherein the light source comprises a laser.

29. The method of claim 27, wherein the light source comprises ultraviolet light.

30. The method of claim 27, wherein the substrate is treated with an organosilane.

31. The method of claim 30, wherein the organosilane further comprises a biologically functionaligroup.

32. The method of claim 31, wherein the biologically functional group comprises a free amino moiety.

33. The method of claim 32, wherein lectin is reacted with the free amino moiety to provide a cell adherent substrate.

34. The method of claim 27, wherein a computer controls the micromirror direction of the light source onto the substrate.

35. The method of claim 27, further comprising a laser in fluid communication with the microchamber or the reagent reservoir.

36. The method of claim 27, further comprising a light amplifier in fluid communication with the microchamber or the reagent reservoir.

37. The method of claim 27, further comprising a mirror in fluid communication with the microchamber or the reagent reservoir.

38. An apparatus, comprising:

one or more microchambers;

wherein the one or more of the microchambers are adapted to contain cells;

one or more fluid conduits in fluid communication with the microchamber;

one or more valves adapted to regulate the flow of a fluid to the one or more microchambers;

one or more reagent reservoirs in fluid communication with the one or more fluid conduits, wherein the valve regulates the flow of fluids between the one or more microchambers and the one or more reagent reservoirs adapted to exchange nutrients, oxygen and remove excretions;

the one or more microchambers adapted to contain cells is substantially planar; and one or more micromirrors arranged to direct light into the microchambers.

39. A cell culturing system, comprising:

one or more nano-scale microchambers for housing cultured cells;

one or more of nano-scale fluid inlets and outlets in fluid communication with the microchambers;

one or more controls to regulate the inlet and the outlet of fluids between the inlets and the outlets and the microchambers; and one or more controls in communication with the microchambers for detecting biological parameters of the cultured cells.

40. An apparatus, comprising:

one or more microchambers;

wherein the one or more of the microchambers are adapted to contain cells;

one or more fluid conduits in fluid communication with the microchamber;

one or more valves adapted to regulate the flow of a fluid to the one or more microchambers;

one or more reagent reservoirs in fluid communication with the one or more fluid conduits, wherein the valve regulates the flow of fluids between the one or more microchambers and the one or more reagent reservoirs adapted to exchange nutrients, oxygen and remove excretions; and the one or more microchambers adapted to contain cells is substantially planar for detecting biological parameters of the cultured cells.

41. A cell culturing system comprising:

a chamber having a bottom substrate for growing cultured cells, the chamber further comprising through-holes for controlled porosity;

a nanoporous semipermeable membrane attached to the substrate; and a top head on the bottom substrate, the head being adapted to provide space for cells to grow on the substrate and to sandwich the membrane between the substrate and the head, wherein fluid exchange occurs across the membrane through the through-holes.

* * * * *